(12) United States Patent
Li et al.

(10) Patent No.: US 8,986,937 B2
(45) Date of Patent: Mar. 24, 2015

(54) COMPOSITIONS AND METHODS FOR DETECTING AUTOANTIBODIES

(75) Inventors: Yunsheng Li, Athens, OH (US); Paul D. Olivo, St. Louis, MO (US); Jaekyung Kim, Athens, OH (US)

(73) Assignee: Quidel Corporation, San Diego, CA (US)

( * ) Notice: Subject to any disclaimer, the term of this patent is extended or adjusted under 35 U.S.C. 154(b) by 275 days.

(21) Appl. No.: 13/228,705

(22) Filed: Sep. 9, 2011

(65) Prior Publication Data
US 2013/0065252 A1    Mar. 14, 2013

(51) Int. Cl.
*G01N 33/53*    (2006.01)
*G01N 33/76*    (2006.01)
*G01N 33/566*    (2006.01)

(52) U.S. Cl.
CPC .............. *G01N 33/76* (2013.01); *G01N 33/566* (2013.01); *G01N 2333/726* (2013.01)
USPC ....................................................... 435/7.2

(58) Field of Classification Search
None
See application file for complete search history.

(56) References Cited

U.S. PATENT DOCUMENTS

| | | | |
|---|---|---|---|
| 6,747,139 B1 | 6/2004 | Rapoport et al. | 536/23.5 |
| 2003/0068801 A1 | 4/2003 | Wood et al. | 435/191 |
| 2008/0187942 A1* | 8/2008 | Brown | 435/8 |
| 2008/0305098 A1 | 12/2008 | Fenning et al. | 424/94.5 |
| 2009/0325177 A1 | 12/2009 | Kohn et al. | 435/6.18 |

OTHER PUBLICATIONS

Arikawa, K. et al. (1985) Blocking Type Antithyrotropin Receptor Antibody in Patients with Nongoitrous Hypothyroidism: Its Incidence and Characteristics of Action, *Journal of Clinical Endocrinology & Metabolism* 60(5), 953-959.
Chiovato, L. et al. (1990) Incidence of Antibodies Blocking Thyrotropin Effect In Vitro in Patients with Euthyroid or Hypothyroid Autoimmune Thyroiditis, *Journal of Clinical Endocrinology & Metabolism* 71(1), 40-45.
Drexhage, H. A. et al. (1981) Thyroid growth-blocking antibodies in primary myxoedema, *Nature* 289(5798), 594-596.
Endo, K. et al. (1978) Detection and Properties of TSH-Binding Inhibitor Immunoglobulins in Patients with Graves' Disease and Hashimoto's Thyroiditis, *Journal of Clinical Endocrinology & Metabolism* 46(5), 734-739.
Iseki, M. et al. (1983) Sequential Serum Measurements of Thyrotropin Binding Inhibitor Immunoglobulin G in Transient Familial Neonatal Hypothyroidism, *Journal of Clinical Endocrinology & Metabolism* 57(2), 384-387.

Kohn, L. D. et al. (2003) Thyrotropin Receptor Autoantibodies (TSHRAbs): Epitopes, Origins and Clinical Significance, *Autoimmunity* 36(6/7), 331-337.
Konishi, J. et al. (1983) Inhibition of Thyrotropin-Induced Adenosine 3'5'-Monophosphate Increase by Immunoglobulins from Patients with Primary Myxedema, *Journal of Clinical Endocrinology & Metabolism* 57(3), 544-549.
Kwast-Welfeld, J. et al. (1989) Identification of rat ovarian nuclear factors that interact with the cAMP-inducible lactate dehydrogenase A subunit promoter, *Journal of Biological Chemistry* 264(12), 6941-6947.
Matsuura, N. et al. (1980) Familial Neonatal Transient Hypothyroidism Due to Maternal TSH-Binding Inhibitor Immunoglobulins, *New England Journal of Medicine* 303(13), 738-741.
Muñiz, L. C. et al. (2006) Transcriptional Regulation of Cyclin D2 by the PKA Pathway and Inducible cAMP Early Repressor in Granulosa Cells, *Biol. Reprod.* 75(2), 279-288.
Roesler, W. J. et al. (1998) Characterization of CCAAT/Enhancer-binding Protein α as a Cyclic AMP-responsive Nuclear Regulator, *Journal of Biological Chemistry* 273(24), 14950-14957.
Sanders, P. et al. (2011) Crystal structure of the TSH receptor (TSHR) bound to a blocking-type TSHR autoantibody, *J. Mol. Endocrinol.* 46(2), 81-99.
Szkudlinski, M. W. et al. (1996) Engineering human glycoprotein hormone superactive analogues, *Nature Biotechnology* 14(10), 1257-1263.
Tahara, K. et al. (1991) Immunoglobulins from Graves' disease patients interact with different sites on TSH receptor/LH-CG receptor chimeras than either TSH or immunoglobulins from idiopathic myxedema patients, *Biochemical and Biophysical Research Communications* 179(1), 70-77.
Tahara, K. et al. (1997) Epitopes for thyroid stimulating and blocking autoantibodies on the extracellular domain of the human thyrotropin receptor, *Thyroid* 7(6), 867-877.
Takasu, N. et al. (1984) Transient Neonatal Hypothyroidism Due to Maternal Immunoglobulins that Inhibit Thyrotropin-Binding and Post-Receptor Processes, *Journal of Clinical Endocrinology & Metabolism* 59(1), 142-146.
Takasu, N. et al. (1987) Evidence for Thyrotropin (TSH)-Blocking Activity in Goitrous Hashimoto's Thyroiditis with Assays Measuring Inhibition of TSH Receptor Binding and TSH-Stimulated Thyroid Adenosine 3',5'-Monophosphate Responses/Cell Growth by Immunoglobulins, *Journal of Clinical Endocrinology & Metabolism* 64(2), 239-245.

* cited by examiner

*Primary Examiner* — Michael Pak
(74) *Attorney, Agent, or Firm* — Medlen & Carroll, LLP

(57) ABSTRACT

The invention provides compositions and methods for detecting thyroid hormone blocking immunoglobulin (TBI). The invention's methods are sensitive and specific for TBI, and may be used for the dual detection of both TBI and TSI. The invention's compositions and methods are useful for the diagnosis of diseases that are associated with the presence of TBI and/or TSI, for monitoring the progress of disease and/or treatment regimens, therapeutics, vaccines, etc., and for assisting clinicians in making treatment decisions.

15 Claims, 12 Drawing Sheets

A.
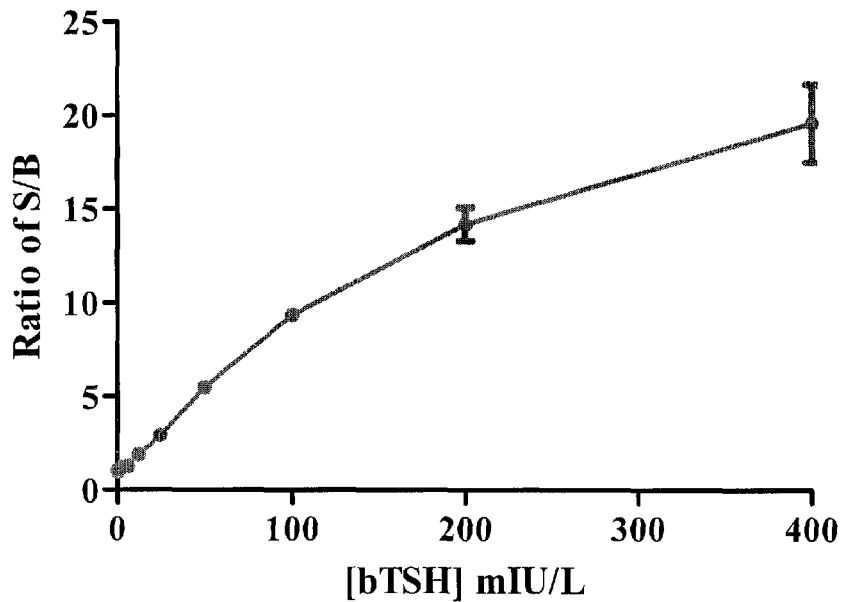
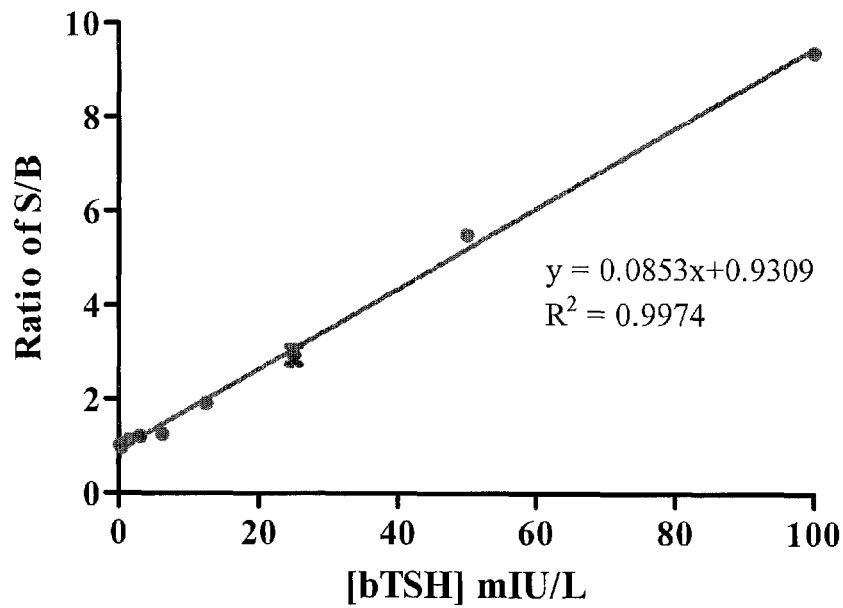
B.
Figure 1

A) Amino acid sequence (SEQ ID NO:01) of the chimeric TSHR contains 730 amino acid residues

```
MRPADLLQLVLLLDLPRDLGGMGCSSPPCECHQEEDFRVTCKDIQRIPSLPPST
QTLKLIETHLRTIPSHAFSNLPNISRIYVSIDVTLQQLESHSFYNLSKVTHIEI
RNTRNLTYIDPDALKELPLLKFLGIFNTGLKMFPDLTKVYSTDIFFILEITDNP
YMTSIPVNAFQGLCNETLTLKLYNNGFTSVQGYAFNGTKLDAVYLNKNKYLTVI
DKDAFGGVYSGPSLLDVSQTSVTALPSKGLEHLKELIARNTWTLKTLPSKEKFT
SLLVATLTYPSHCCAFSNLPKKEQNFSFSIFENFSKQCESTVRKADNETLYSAI
FEENELSGWDELKNPQEETLQAFDSHYDYTICGDSEDMVCTPKSDEFNPCEDIM
GYKFLRIVVWFVSLLALLGNVFVLLILLTSHYKLNVPRFLMCNLAFADFCMGMY
LLLIASVDLYTHSEYYNHAIDWQTGPGCNTAGFFTVFASELSVYTLTVITLERW
YAITFAMRLDRKIRLRHACAIMVGGWVCCFLLALLPLVGISSYAKVSICLPMDT
ETPLALAYIVFVLTLNIVAFVIVCCCYVKIYITVRNPQYNPGDKDTKIAKRMAV
LIFTDFICMAPISFYALSAILNKPLITVSNSKILLVLFYPLNSCANPFLYAIFT
KAFQRDVFILLSKFGICKRQAQAYRGQRVPPKNSTDIQVQKVTHDMRQGLHNME
DVYELIENSHLTPKKQGQISEEYMQTVL
```

B) DNA sequence (SEQ ID NO:02) of the chimeric TSHR contains 2193 bases, which include the stop codon

```
ATGAGGCCGGCGGACTTGCTGCAGCTGGTGCTGCTGCTCGACCTGCCCAGGGAC
CTGGGCGGAATGGGGTGTTCGTCTCCACCCTGCGAGTGCCATCAGGAGGAGGAC
TTCAGAGTCACCTGCAAGGATATTCAACGCATCCCCAGCTTACCGCCCAGTACG
CAGACTCTGAAGCTTATTGAGACTCACCTGAGAACTATTCCAAGTCATGCATTT
TCTAATCTGCCCAATATTTCCAGAATCTACGTATCTATAGATGTGACTCTGCAG
CAGCTGGAATCACACTCCTTCTACAATTTGAGTAAAGTGACTCACATAGAAATT
CGGAATACCAGGAACTTAACTTACATAGACCCTGATGCCCTCAAAGAGCTCCCC
CTCCTAAAGTTCCTTGGCATTTTCAACACTGGACTTAAAATGTTCCCTGACCTG
ACCAAAGTTTATTCCACTGATATATTCTTTATACTTGAAATTACAGACAACCCT
TACATGACGTCAATCCCTGTGAATGCTTTTCAGGGACTATGCAATGAAACCTTG
ACACTGAAGCTGTACAACAATGGCTTTACTTCAGTCCAAGGATATGCTTTCAAT
GGGACAAAGCTGGATGCTGTTTACCTAAACAAGAATAAATACCTGACAGTTATT
GACAAAGATGCATTTGGAGGAGTATACAGTGGACCAAGCTTGCTGGACGTGTCT
CAAACCAGTGTCACTGCCCTTCCATCCAAAGGCCTGGAGCACCTGAAGGAACTG
ATAGCAAGAAACACCTGGACTCTTAAGACACTGCCCTCCAAAGAAAAATTCACG
AGCCTCCTGGTCGCCACGCTGACCTACCCCAGCCACTGCTGCGCCTTCAGTAAT
TTGCCGAAGAAAGAACAGAATTTTTCATTTTCCATTTTTGAAAACTTCTCCAAA
CAATGCGAAAGCACAGTTAGAAAGCAGATAACGAGACGCTTTATTCCGCCATC
TTTGAGGAGAATGAACTCAGTGGCTGGGATGAGCTCAAAAACCCCCAGGAAGAG
ACTCTACAAGCTTTTGACAGCCATTATGACTACACCATATGTGGGACAGTGAA
```

Figure 2

```
GACATGGTGTGTACCCCCAAGTCCGATGAGTTCAACCCGTGTGAAGACATAATG
GGCTACAAGTTCCTGAGAATTGTGGTGTGGTTCGTTAGTCTGCTGGCTCTCCTG
GGCAATGTCTTTGTCCTGCTTATTCTCCTCACCAGCCACTACAAACTGAACGTC
CCCCGCTTTCTCATGTGCAACCTGGCCTTTGCGGATTTCTGCATGGGGATGTAC
CTGCTCCTCATCGCCTCTGTAGACCTCTACACTCACTCTGAGTACTACAACCAT
GCCATCGACTGGCAGACAGGCCCTGGGTGCAACACGGCTGGTTTCTTCACTGTC
TTTGCAAGCGAGTTATCGGTGTATACGCTGACGGTCATCACCCTGGAGCGCTGG
TATGCCATCACCTTCGCCATGCGCCTGGACCGGAAGATCCGCCTCAGGCACGCA
TGTGCCATCATGGTTGGGGGCTGGGTTTGCTGCTTCCTTCTCGCCCTGCTTCCT
TTGGTGGGAATAAGTAGCTATGCCAAAGTCAGTATCTGCCTGCCCATGGACACC
GAGACCCTCTTGCTCTGGCATATATTGTTTTTGTTCTGACGCTCAACATAGTT
GCCTTCGTCATCGTCTGCTGCTGTTATGTGAAGATCTACATCACAGTCCGAAAT
CCGCAGTACAACCCAGGGGACAAAGATACCAAAATTGCCAAGAGGATGGCTGTG
TTGATCTTCACCGACTTCATATGCATGGCCCCAATCTCATTCTATGCTCTGTCA
GCAATTCTGAACAAGCCTCTCATCACTGTTAGCAACTCCAAAATCTTGCTGGTA
CTCTTCTATCCACTTAACTCCTGTGCCAATCCATTCCTCTATGCTATTTTCACC
AAGGCCTTCCAGAGGGATGTGTTCATCCTACTCAGCAAGTTTGGCATCTGTAAA
CGCCAGGCTCAGGCATACCGGGGGCAGAGGGTTCCTCCAAAGAACAGCACTGAT
ATTCAGGTTCAAAAGGTTACCCACGACATGAGGCAGGGTCTCCACAACATGGAA
GATGTCTATGAACTGATTGAAAACTCCATCTAACCCCAAAGAAGCAAGGCCAA
ATCTCAGAAGAGTATATGCAAACGGTTTTGTAA
```

C) Amino acid sequence (SEQ ID NO:03) of firefly luciferase contains 550 amino acids

```
MEDAKNIKKGPAPFYPLEDGTAGEQLHKAMKRYALVPGTIAFTDAHIEVNITYA
EYFEMSVRLAEAMKRYGLNTNHRIVVCSENSLQFFMPVLGALFIGVAVAPANDI
YNERELLNSMNISQPTVVFVSKKGLQKILNVQKKLPIIQKIIIMDSKTDYQGFQ
SMYTFVTSHLPPGFNEYDFVPESFDRDKTIALIMNSSGSTGLPKGVALPHRTAC
VRFSHARDPIFGNQIIPDTAILSVVPFHHGFGMFTTLGYLICGFRVVLMYRFEE
ELFLRSLQDYKIQSALLVPTLFSFFAKSTLIDKYDLSNLHEIASGGAPLSKEVG
EAVAKRFHLPGIRQGYGLTETTSAILITPEGDDKPGAVGKVVPFFEAKVVDLDT
GKTLGVNQRGELCVRGPMIMSGYVNNPEATNALIDKDGWLHSGDIAYWDEDEHF
FIVDRLKSLIKYKGYQVAPAELESILLQHPNIFDAGVAGLPDDDAGELPAAVVV
LEHGKTMTEKEIVDYVASQVTTAKKLRGGVVFVDEVPKGLTGKLDARKIREILI
KAKKGGKSKL
```

Figure 2

D) DNA sequence (SEQ ID NO:04) of the chimeric TSHR contains 1653 bases, which include the stop codon

```
ATGGAAGACGCCAAAAACATAAAGAAAGGCCCGGCGCCATTCTATCCTCTAGAG
GATGGAACCGCTGGAGAGCAACTGCATAAGGCTATGAAGAGATACGCCCTGGTT
CCTGGAACAATTGCTTTTACAGATGCACATATCGAGGTGAACATCACGTACGCG
GAATACTTCGAAATGTCCGTTCGGTTGGCAGAAGCTATGAAACGATATGGGCTG
AATACAAATCACAGAATCGTCGTATGCAGTGAAAACTCTCTTCAATTCTTTATG
CCGGTGTTGGGCGCGTTATTTATCGGAGTTGCAGTTGCGCCCGCGAACGACATT
TATAATGAACGTGAATTGCTCAACAGTATGAACATTTCGCAGCCTACCGTAGTG
TTTGTTTCCAAAAAGGGGTTGCAAAAAATTTTGAACGTGCAAAAAAAATTACCA
ATAATCCAGAAAATTATTATCATGGATTCTAAAACGGATTACCAGGGATTTCAG
TCGATGTACACGTTCGTCACATCTCATCTACCTCCCGGTTTTAATGAATACGAT
TTTGTACCAGAGTCCTTTGATCGTGACAAAACAATTGCACTGATAATGAATTCC
TCTGGATCTACTGGGTTACCTAAGGGTGTGGCCCTTCCGCATAGAACTGCCTGC
GTCAGATTCTCGCATGCCAGAGATCCTATTTTGGCAATCAAATCATTCCGGAT
ACTGCGATTTTAAGTGTTGTTCCATTCCATCACGGTTTTGGAATGTTTACTACA
CTCGGATATTTGATATGTGGATTTCGAGTCGTCTTAATGTATAGATTTGAAGAA
GAGCTGTTTTTACGATCCCTTCAGGATTACAAAATTCAAAGTGCGTTGCTAGTA
CCAACCCTATTTTCATTCTTCGCCAAAAGCACTCTGATTGACAAATACGATTTA
TCTAATTTACACGAAATTGCTTCTGGGGGCGCACCTCTTTCGAAAGAAGTCGGG
GAAGCGGTTGCAAAACGCTTCCATCTTCCAGGGATACGACAAGGATATGGGCTC
ACTGAGACTACATCAGCTATTCTGATTACACCCGAGGGGGATGATAAACCGGGC
GCGGTCGGTAAAGTTGTTCCATTTTTTGAAGCGAAGGTTGTGGATCTGGATACC
GGGAAAACGCTGGGCGTTAATCAGAGAGGCGAATTATGTGTCAGAGGACCTATG
ATTATGTCCGGTTATGTAAACAATCCGGAAGCGACCAACGCCTTGATTGACAAG
GATGGATGGCTACATTCTGGAGACATAGCTTACTGGGACGAAGACGAACACTTC
TTCATAGTTGACCGCTTGAAGTCTTTAATTAAATACAAAGGATATCAGGTGGCC
CCCGCTGAATTGGAATCGATATTGTTACAACACCCCAACATCTTCGACGCGGGC
GTGGCAGGTCTTCCCGACGATGACGCCGGTGAACTTCCCGCCGCCGTTGTTGTT
TTGGAGCACGGAAAGACGATGACGGAAAAGAGATCGTGGATTACGTCGCCAGT
CAAGTAACAACCGCGAAAAGTTGCGCGGAGGAGTTGTGTTTGTGGACGAAGTA
CCGAAAGGTCTTACCGGAAAACTCGACGCAAGAAAAATCAGAGAGATCCTCATA
AAGGCCAAGAAGGGCGGAAAGTCCAAATTGTAA
```

Figure 2

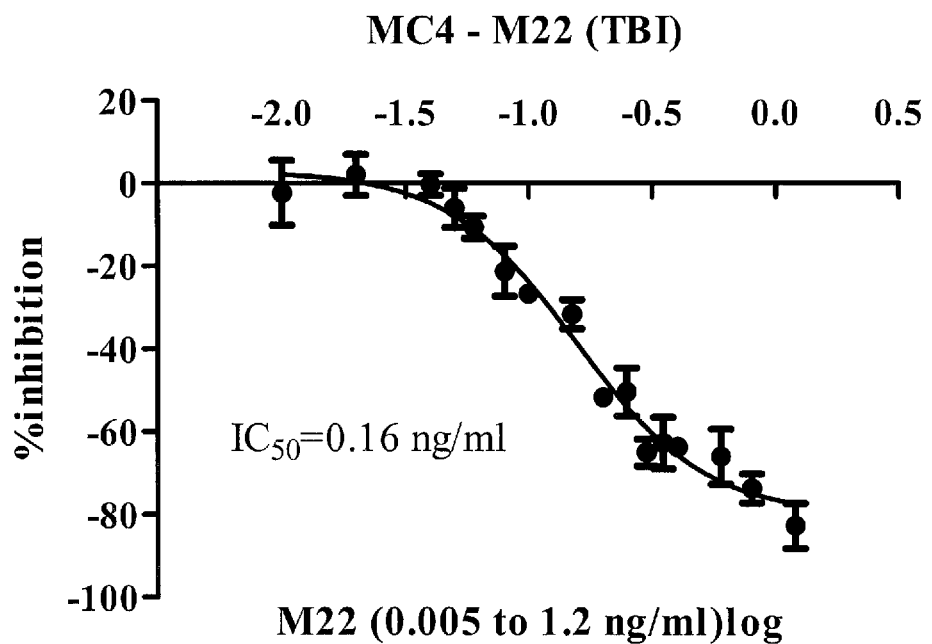
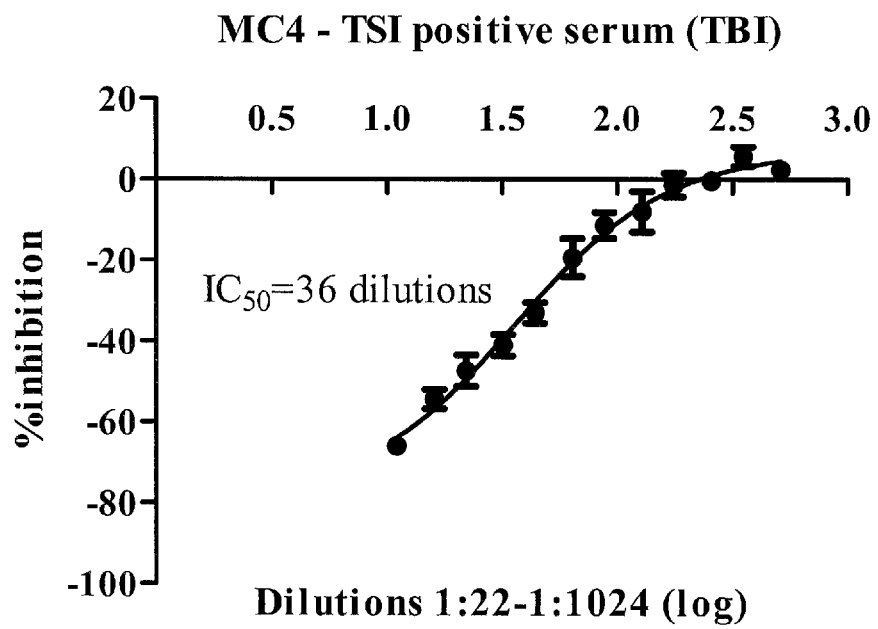
Figure 6

COMPOSITIONS AND METHODS FOR DETECTING AUTOANTIBODIES

FIELD OF THE INVENTION

The invention provides compositions and methods for detecting thyroid hormone blocking immunoglobulin (TBI). The invention's methods are sensitive and specific for TBI, and may be used for the dual detection of both TBI and thyroid stimulating immunoglobulin (TSI). The invention's compositions and methods are useful for the diagnosis of diseases that are associated with the presence of TBI and/or TSI, for monitoring the progress of disease and/or treatment regimens, therapeutics, vaccines, etc., and for assisting clinicians in making treatment decisions.

BACKGROUND OF THE INVENTION

A significant number of the population suffers from thyroid diseases, including Graves' disease, Hashimoto's thyroiditis, hyperthyroidism, hypothyroidism (including neonatal hypothyroidism), nongoitrous hypothyroidism, Euthyroid or hypothyroid autoimmune thyroiditis, primary myxedema and idiopathic myxedema. These diseases involve the action of autoantibodies (thyroid blocking immunoglobulin (TBI) and/or thyroid stimulating immunoglobulin (TSI)) that recognize and bind to receptors present on the thyroid gland, resulting in undesirable changes in the production of thyroid hormone.

While diagnostic techniques are available for some of these diseases, these techniques are nonetheless cumbersome, laborious, and lack sufficient sensitivity and/or specificity.

Thus, there remains a need for compositions and methods for detecting thyroid hormone blocking immunoglobulin (TBI) and/or thyroid stimulating immunoglobulin (TSI), that are sensitive and specific, and that may be used for the dual detection of both TBI and TSI.

SUMMARY OF THE INVENTION

The invention provides a method for detecting thyroid hormone blocking immunoglobulin (TBI) in a test sample, comprising a) providing i) transgenic cells stably transfected with one or more expression vector comprising a 1) a reporter gene operably linked to a cAMP-inducible promoter, and 2) a chimeric TSH receptor (TSHR) gene operably linked to a constitutive promoter, wherein the cells express a chimeric TSHR on the cell membrane, ii) thyroid stimulating hormone (TSH), iii) a control sample, and iv) a test sample, b) contacting the transgenic cells and the TSH with i) the control sample to produce a first sample, and ii) the test sample to produce a second sample, wherein the contacting is under conditions for binding of the TSH to the chimeric TSHR, and c) measuring the level of expression of the reporter gene in the first sample and in the second sample, wherein a reduced level of expression of the reporter gene in the second sample compared to the first sample indicates the presence of TBI in the test sample. In one embodiment, the method of detecting TBI has a TBI $IC_{50}$ from 5 fold to 15 fold smaller than the TBI $IC_{50}$ when detecting TBI in the method that comprises substituting the transgenic cells that express the chimeric TSHR with cells that express a wild type TSHR. In another embodiment, the method of detecting TBI has a TBI $IC_{50}$ from 10 fold to 30 fold smaller than the TBI $IC_{50}$ when detecting TBI in a method that comprises detecting specific binding of TBI with anti-TBI monoclonal antibody. In a further embodiment, the method further comprises detecting a reduced level of expression of the reporter gene in the second sample compared to the first sample. In yet another embodiment, the method further comprises determining the level of TBI in the test sample by comparing a) the level of expression of the reporter gene after the contacting with the test sample, with b) the level of expression of the reporter gene after contacting the transgenic cells with one or more standard samples, each containing a known concentration of TSH. In a further embodiment, the method is TBI specific. In another embodiment, the TSH has a concentration of less than 100 mIU/ml. In an alternative embodiment, expression of the reporter gene comprises expression of a bioluminescence protein. In a further embodiment, the bioluminescence protein comprises *Renilla* luciferase amino acid sequence SEQ ID NO:03. In another embodiment, the transgenic cells comprise a cell selected from CHO-MC4 cell and RD-MC4 cell. In some embodiments, the TSH is replaced with a thyroid stimulating monoclonal antibody and/or with a thyroid stimulating polyclonal antibody.

The invention additionally provides a method for detecting thyroid hormone blocking immunoglobulin (TBI) and thyroid hormone stimulating immunoglobulin (TSI) in a test sample, comprising a) providing i) transgenic cells stably transfected with one or more expression vector comprising a 1) a reporter gene operably linked to a cAMP-inducible promoter, and 2) a chimeric TSH receptor (TSHR) gene operably linked to a constitutive promoter, wherein the cells express a chimeric TSHR on the cell membrane, ii) thyroid stimulating hormone (TSH), iii) a control sample, and iv) a test sample, b) contacting the transgenic cells and the TSH with i) the control sample to produce a first sample, and ii) the test sample to produce a second sample, wherein the contacting is under conditions for binding of the TSH to the chimeric TSHR, and c) measuring the level of expression of the reporter gene in the transgenic cells before the contacting and after the contacting, wherein i) a reduced level of expression of the reporter gene in the second sample compared to the first sample indicates the presence of TBI in the test sample, and ii) an increased level of expression of the reporter gene in the second sample compared to the first sample indicates the presence of TSI in the test sample. In one embodiment, the method further comprises detecting a reduced level of expression of the reporter gene in the second sample compared to the first sample. In a particular embodiment, the transgenic cells comprise a cell selected from CHO-MC4 cell and RD-MC4 cell.

Also provided herein is a kit comprising a) transgenic cells stably transfected with one or more expression vector comprising a i) a reporter gene operably linked to a cAMP-inducible promoter, and ii) a chimeric TSH receptor (TSHR) gene operably linked to a constitutive promoter, wherein the cells express a chimeric TSHR on the cell membrane, and b) instructions for using the transgenic cells for detecting thyroid hormone blocking immunoglobulin (TBI). In one embodiment, the kit further comprises a positive control sample that contains thyroid hormone blocking immunoglobulin (TBI). In another embodiment, the kit further comprises thyroid stimulating hormone (TSH). In yet a further embodiment, the kit further comprises instructions for detecting thyroid hormone stimulating immunoglobulin (TSI) in a test sample. In another embodiment, the kit further comprises a positive control sample that contains thyroid hormone stimulating immunoglobulin (TSI).

BRIEF DESCRIPTION OF THE DRAWINGS

FIG. 1 shows the bTSH dose response curves using the CHO-MC4 cells.

FIG. 2 shows (A) amino acid sequence (SEQ ID NO:01) of the chimeric TSHR that contains 730 amino acid residues, (B)

DNA sequence (SEQ ID NO:02) of the chimeric TSHR that contains 2193 bases, which include the stop codon, (C) Amino acid sequence (SEQ ID NO:03) of the *Renilla* luciferase that contains 550 amino acids, and (D) DNA sequence (SEQ ID NO:04) of the chimeric TSHR that contains 1653 bases, which include the stop codon.

Figure 3:
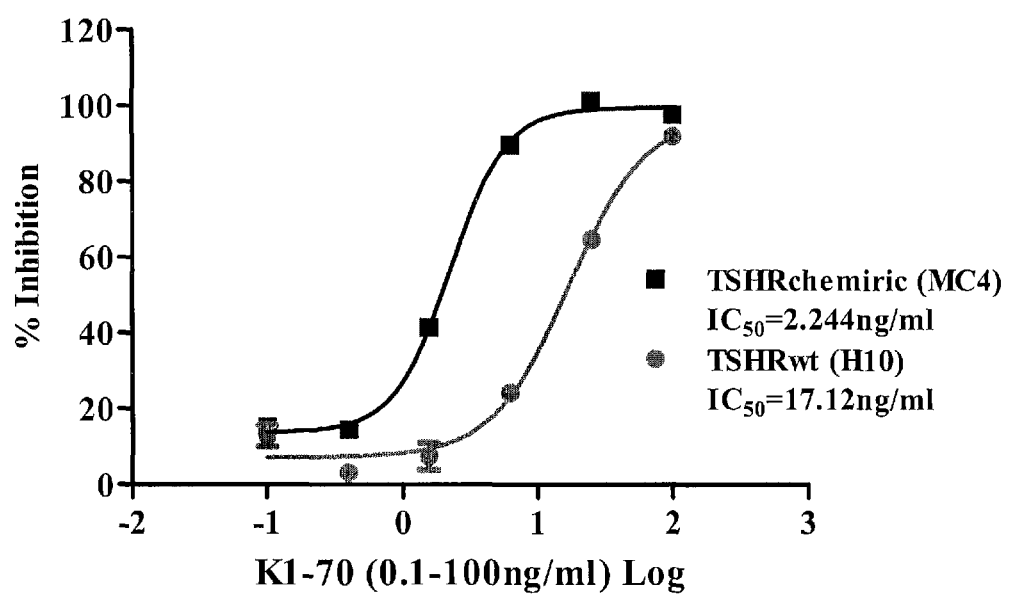

FIG. 3: Comparison of detection sensitivity of Thyroid Blocking Immunoglobulin (TBI) assays with thyroid blocking monoclonal antibody (MAb) K1-70 in CHO-MC4 and TSHRwt cells (H10).

Figure 4:
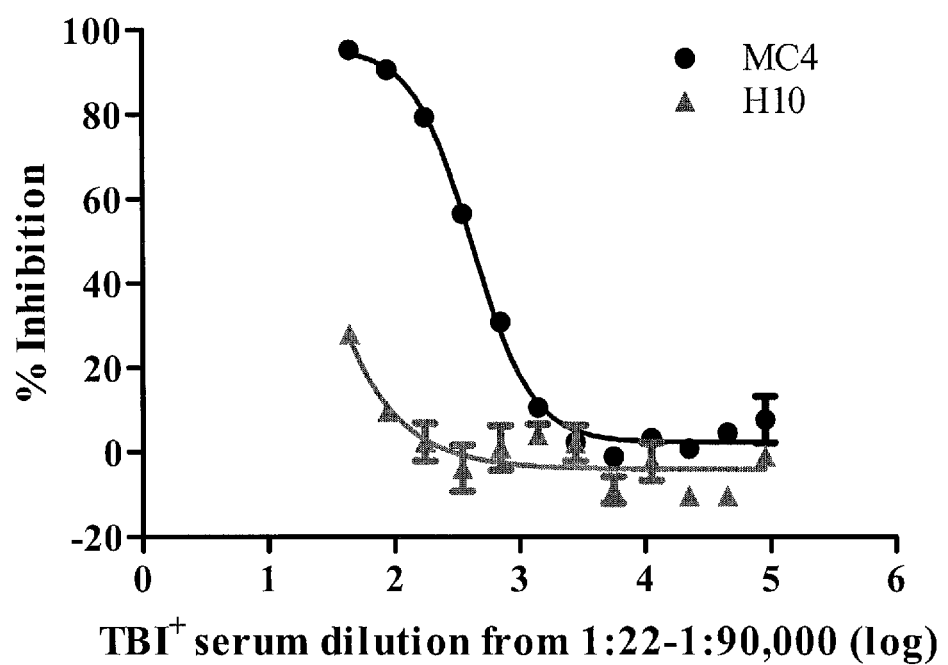

FIG. 4: Comparison of detection sensitivity of TBI assay with a blocking antibody containing serum in MC4 and H10 cells.

Figure 5:
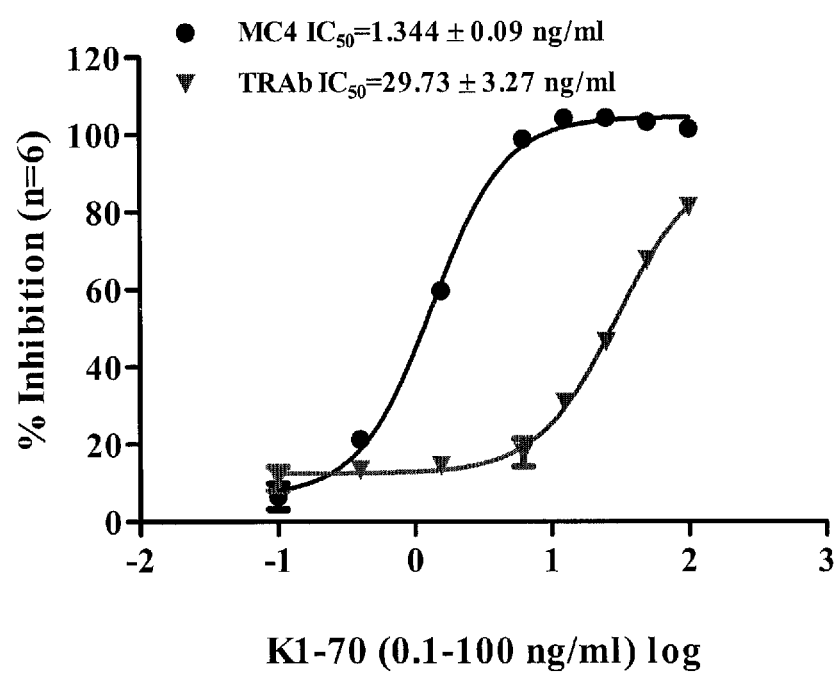

FIG. 5: Comparison of thyroid blocking monoclonal antibody K1-70 dose response curves: TBI assay versus TRAb assays.

FIG. 6: TBI assay with serial diluted (A) thyroid stimulating monoclonal antibody M22 or (B) TSI positive patient serum.

Figure 7:
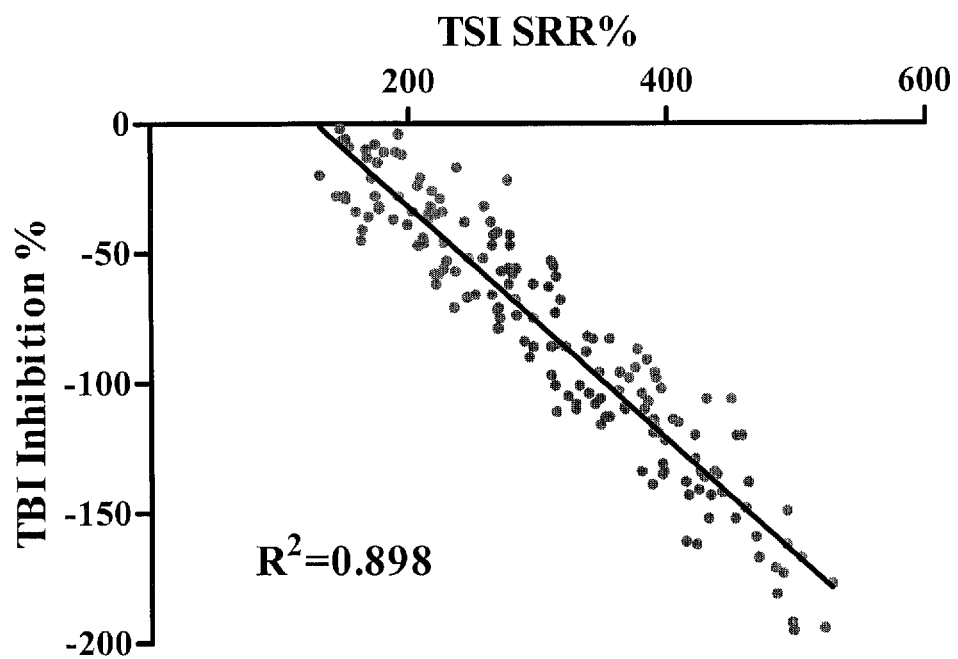

FIG. 7: Correlation between the TSI and TBI assay on 171 TSI positive serum samples.

Figure 8:
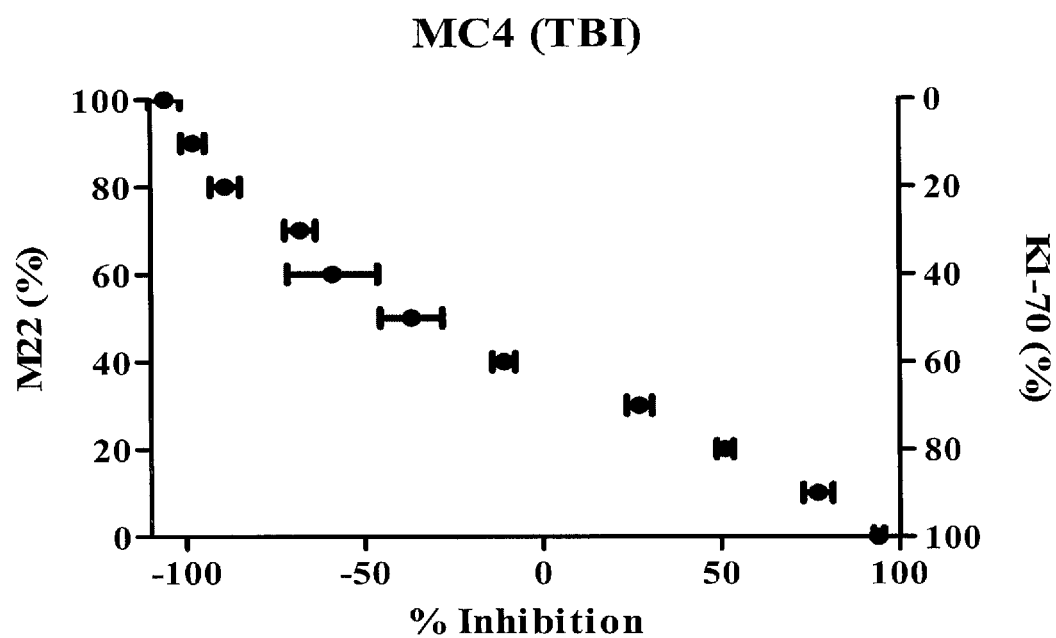

FIG. 8: TBI assay with different ratios of the thyroid stimulating monoclonal antibody M22 and thyroid blocking monoclonal antibody K1-70.

Figure 9:
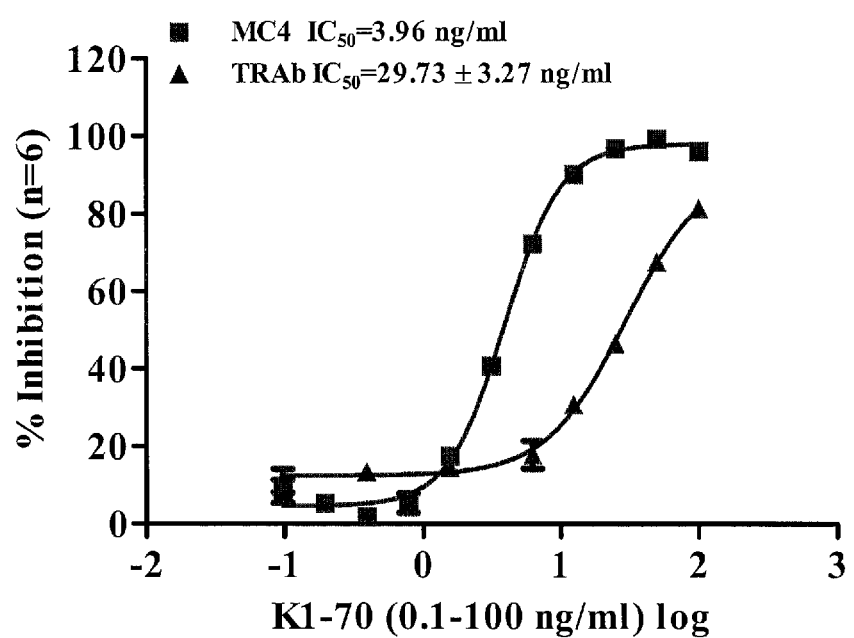

FIG. 9: TBI assay performed using M22 monoclonal antibody instead of bTSH.

Figure 10:
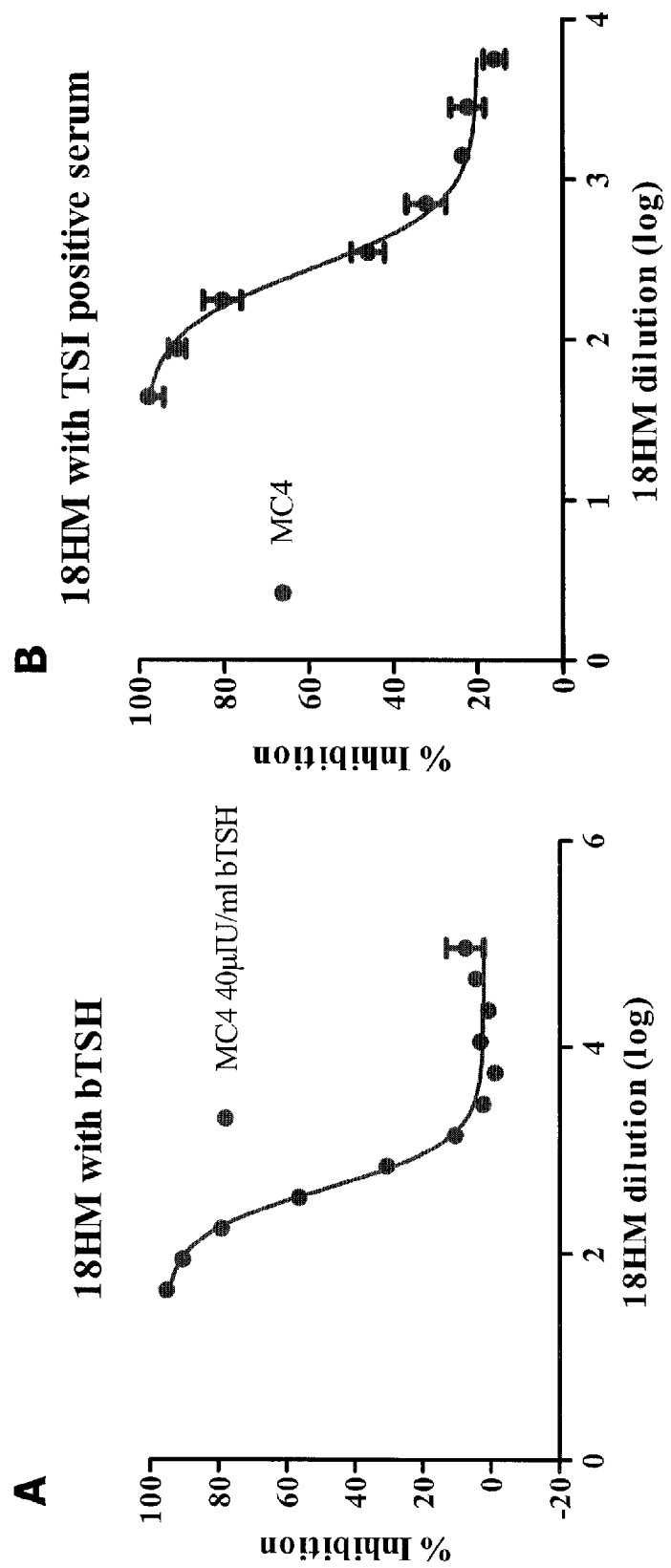

FIG. 10: TBI assay with dilutions of sample 18HM bTSH versus TSI-positive serum. Serum sample 18HM (TRAb positive and TSI negative) was diluted from 1:44 to 1:90112 in normal serum and then mixed with A. bTSH (40 mIU/ml) or B. mixed with TSI positive serum (4.54 ml/well).

DEFINITIONS

To facilitate understanding of the invention, a number of terms are defined below.

The term "transgenic" when used in reference to a cell refers to a cell which contains a transgene, or whose genome has been altered by the introduction of a "transgene." Transgenic cells may be produced by several methods including the introduction of a "transgene" comprising nucleic acid (usually DNA) into a target cell or integration of the transgene into a chromosome of a target cell by way of human intervention.

The term "transgene" as used herein refers to any nucleic acid sequence which is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Chimeric," "fusion" and "hybrid" sequence (e.g., when in reference to an amino acid sequence and/or nucleotide sequence) refers to a sequence containing parts from different origins. In one embodiment, the parts may be from different proteins and/or genomic sequences from the same organism, same tissue, same cell, same virus, etc. In one embodiment, the chimeric protein is a recombinant protein that is produced by expressing operably linked nucleotide sequences that encode the amino acid sequences. For example, a "chimeric TSH receptor", "chimeric TSHR", and "chimeric MC4 receptor" interchangeably refer to a TSHR containing amino acid sequences from different organisms. In one embodiment, the chimeric TSHR is exemplified by a human TSHR (hTSHR) protein sequence in which amino acid residues 262-335 of the hTSHR are substituted with the corresponding 73 amino acid residues from a rat luteinizing hormone chorionic gonadotropin (LH/CG) receptor, as previously described (U.S. Pat. Appl. Publication no. US 2008-0187942, published on Aug. 7, 2008). In a preferred embodiment, the chimeric MC4 receptor is exemplified by the 730-amino acid sequence SEQ ID NO:01 (FIG. 2A) that is encoded by the DNA sequence (SEQ ID NO:02) (2193 base pairs, including the stop codon).

"MC-4" cell refers to a cell that expresses a chimeric TSH receptor. For example, a "CHO-MC4" cell and an "RD-MC4" cell refer to a transgenic Chinese Hamster Ovary cell and to a transgenic human Rhabdomyosarcoma cell, respectively, that express a chimeric TSH receptor, as previously described (U.S. Pat. Appl. Publication No. US 2008-0187942, published on Aug. 7, 2008).

"Reporter sequence" and "marker sequence" are used interchangeably to refer to a DNA, RNA, and/or polypeptide sequence that is detectable in any detection system, including, but not limited to enzyme (e.g., ELISA, as well as enzyme-based histochemical assays), fluorescent, and luminescent systems. Exemplary reporter genes include, for example, β-glucuronidase gene, green fluorescent protein (GFP) gene, *E. coli* β-galactosidase (LacZ) gene, *Halobacterium* β-galactosidase gene, *Neuropsora* tyrosinase gene, human placental alkaline phosphatase gene, and chloramphenicol acetyltransferase (CAT) gene, Aequorin (jellyfish bioluminescence) gene, Firefly luciferase (EC 1.13.12.7) form the American firefly, *Photinus pyralis*, *Renilla* luciferase (EC 1.13.12.5) from the sea pansy *Renilla reniformis*, and Bacterial luciferase (EC 1.14.14.3) from *Photobacterium fischeri*. In a preferred embodiment, the luciferase gene encodes the *Renilla* luciferase amino acid sequence SEQ ID NO:03.

"Bioluminescence gene" refers to a reporter gene encoding a protein that catalyzes a luminescent reaction, such as Aequorin (jellyfish) bioluminescence gene and luciferase gene.

"Luciferase gene" refers to a gene that encodes a monooxygenase enzyme that catalyzes a luminescent reaction, such as Firefly luciferase (EC 1.13.12.7) form the American firefly, *Photinus pyralis*, *Renilla* luciferase (EC 1.13.12.5) from the sea pansy *Renilla reniformis*, and Bacterial luciferase (EC 1.14.14.3) from *Photobacterium fischeri*. In a preferred embodiment, the luciferase gene encodes the *Renilla* luciferase amino acid sequence SEQ ID NO:03.

"Promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

"Inducible promoter" refers to a promoter that is capable of directing a higher level of transcription of an operably linked nucleic acid sequence in the presence of a stimulus (e.g., heat shock, chemicals, etc.) compared to in the absence of the stimulus. For example, a "cAMP-inducible promoter" refers to a promoter that is capable of directing a higher level of transcription of an operably linked nucleic acid sequence in the presence of cAMP compared to in the absence of cAMP. Exemplary cAMP-inducible promoters include the PEPCK promoter (Roesler et al. (1998) The Journal of Biological Chemistry, 273, 14950-14957); promoters containing the cAMP-responsive element (CRE) that is located at position—294 with respect to the translation initiation site of the human cyclin D2 promoter (Muñiz et al. (2006) Biology of Reproduction 75(2): 279-288); and promoters containing the cAMP-responsive element (CRE) of the lactate dehydrogenase A subunit promoter (Welfeld et al. (1989) J. Biol. Chem. 264(12):6941-7. In a preferred embodiment, the exemplary cAMP-inducible promoters comprise a 236 nucleotide glycoprotein hormone alpha subunit promoter, which contains a cyclic AMP (cAMP) regulatory element (CRE) (AF401991), as described in U.S. Pat. Appl. Publication no. US 2008-0187942, published on Aug. 7, 2008.

"Constitutive promoter" refers to a promoter that directs continuous transcription of an operably linked nucleic acid sequence in the absence of a stimulus (e.g., heat shock, chemicals, etc.). Constitutive promoters include those from *E. coli* ($\sigma70$, $\sigma S$, $\sigma32$, $\sigma54$, and $\sigma A$) promoters, *B. subtilis* $\sigma B$ promoters, *Salmonella* Pspv2 and Pspv promoters, bacteriophage T7 (recognized by the T7 RNA Polymerase), bacteriophage SP6 (recognized by the SP6 RNA Polymerase), yeast (pAdh, ADH1, cyc100, pPGK1, pCYC) promoters, and SV40 promoter. In a preferred embodiment, the constitutive promoter is an SV40 promoter.

"Stable transformation" and "stable transfection" and grammatical equivalents refer to the introduction and integration of one or more nucleotide sequence of interest into the genome of a cell. Thus, a "stable transformant" is distinguished from a transient transformant in that, whereas genomic DNA from the stable transformant contains one or more heterologous nucleotide sequences of interest, genomic DNA from the transient transformant does not contain the heterologous nucleotide sequence of interest. Stable transformation of a cell may be detected by Southern blot hybridization of genomic DNA of the cell with nucleic acid sequences that are capable of binding to one or more of the nucleotide sequences of interest. Alternatively, stable transformation of a cell may also be detected by the polymerase chain reaction of genomic DNA of the cell to amplify the nucleotide sequence of interest.

"TBI", "thyroid blocking immunoglobulin", "thyroid blocking antibody" ("TBAb"), "thyrotropin receptor blocking antibody", "TSH binding inhibition immunoglobulin", "thyrotropin binding inhibiting immunoglobulin" ("TBII"), "blocking thyrotropin receptor antibody" ("TSHRAb") are used interchangeably to refer to an antibody that specifically binds to epitopes on the thyroid stimulating hormone receptor (also referred to as "TSH receptor" or "TSHR" or "thyrotropin receptor") and that inhibits (i.e., reduces) binding of this receptor to its thyroid stimulating hormone (TSH) ligand. TBI is exemplified by K1-70 monoclonal antibody.

"TSI", "thyroid stimulating immunoglobulin", "thyroid stimulating antibody" ("TSAb"), "stimulating thyrotropin receptor antibody" ("TSHRAb") are used interchangeably to refer to an antibody that specifically binds to epitopes on the thyroid stimulating hormone receptor (also referred to as "TSH receptor" or "TSHR" or "thyrotropin receptor") and that stimulates (i.e., increases) binding of this receptor to its thyroid stimulating hormone (TSH) ligand. The thyroid stimulating antibody may be monoclonal or polyclonal. Thus, a "thyroid stimulating monoclonal antibody" and "monoclonal thyroid stimulating antibody" interchangeably refer to a monoclonal thyroid stimulating antibody that binds to an epitope of TSHR within the TSH binding site, as exemplified by M22 antibody.

"Thyroid stimulating hormone" ("TSH") is exemplified by human TSH (hTSH) and bovine TSH (bTSH) having an exemplary amino acid sequence as previously described (Szkudlinski et al. (1996) Nat. Biotechnol. 14:1257-1263).

"Antibody" and "immunoglobulin" refer to a glycoprotein (e.g., IgG, IgM, IgA, IgE, IgD, etc.) and/or portion thereof that contains a "variable domain" (also referred to as the "$F_v$ region") for binding to antigens. In one embodiment, the antibody is a "polyclonal antibody," i.e., an immunoglobulin produced by more than a single clone of plasma cells (e.g., B-lymphocytes). In another embodiment, the antibody is a "monoclonal antibody" ("MAb"), i.e., an immunoglobulin that is produced by a single clone of hybridoma cells. In another embodiment, the antibody is an "autoantibody" produced by a subject, and is capable of binding with an antigen ("self" antigen) produced the same subject.

"Antigen" and "immunogen" when made in reference to a molecule, refer to any substance that is capable of inducing a specific humoral immune response (including eliciting a soluble antibody response) and/or cell-mediated immune response (including eliciting a CTL response).

"Specifically binds" and "specific binding" when made in reference to the binding of antibody to a molecule (e.g., peptide) or binding of a cell (e.g., T-cell) to a peptide, refer to an interaction of the antibody or cell with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will reduce the amount of labeled A bound to the antibody. In one embodiment, the level of binding of an antibody to a molecule is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

"Sample" and "specimen" as used herein are used in their broadest sense to include any composition, such as a chemical reaction mixture, a composition from a biological and/or environmental source, as well as sampling devices (e.g., swabs) that have come into contact with these compositions. "Biological samples" include those obtained from a subject, including body fluids (such as urine, blood, plasma, fecal matter, cerebrospinal fluid (CSF), semen, sputum, and saliva), as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. These examples are illustrative, and are not to be construed as limiting the sample types applicable to the present invention.

A "control sample" refers to a sample used for comparing to another sample by maintaining the same conditions in the control and other samples, except in one or more particular variable in order to infer a causal significance of this varied one or more variable on a phenomenon. For example, a "positive control sample" is a control sample in which the phenomenon is expected to occur. For example, a "negative control sample" is a control sample in which the phenomenon is not expected to occur.

A "standard sample" refers to a sample that is used as a reference for evaluating another sample (such as a test sample). For example, one or more standard samples, each containing a known concentration and/or amount of TSH, may be used as a reference for evaluating the concentration and/or amount of TSH in a test sample.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a thyroid stimulating hormone (TSH) ligand to its thyroid stimulating hormone receptor (TSH receptor), specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a thyroid stimulating hormone (TSH) ligand to its thyroid stimulating hormone receptor (TSH receptor), specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The term "not substantially reduced" when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a thyroid stimulating hormone (TSH) ligand to its thyroid stimulating hormone receptor (TSH receptor), specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), means that the quantity of molecule, cell and/or phenomenon in the first sample (or in the first subject) is from 91% to 100% of the quantity in the second sample (or in the second subject).

The terms "alter" and "modify" when in reference to the level of any molecule and/or phenomenon refer to an increase and/or decrease.

"Substantially the same" when in reference to the level of any molecule (e.g., amino acid sequence, and nucleic acid sequence, antibody, etc.), cell, virus, and/or phenomenon (e.g., level of expression of a gene, disease symptom, level of binding of two molecules such as binding of a thyroid stimulating hormone (TSH) ligand to its thyroid stimulating hormone receptor (TSH receptor), specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell and/or phenomenon in the first sample (or in the first subject) is not different from the quantity in the second sample (or in the second subject) using any art-accepted statistical method of analysis. In one embodiment, the quantity of molecule, cell and/or phenomenon in the first sample (or in the first subject) is from 90% to 100% (e.g., 90%, 91%, 92%, 93%, 94%, 95%, 96%, 97%, 98%, 99%, and 100%) of the quantity in the second sample (or in the second subject).

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides compositions and methods for detecting thyroid hormone blocking immunoglobulin (TBI). The invention's methods are sensitive and specific for TBI, and may be used for the dual detection of both TBI and thyroid stimulating immunoglobulin (TSI). The invention's compositions and methods are useful for the diagnosis of diseases that are associated with the presence of TBI and/or TSI, for monitoring the progress of disease and/or treatment regimens, therapeutics, vaccines, etc., and for assisting clinicians in making treatment decisions.

The invention is further described under (A) Assays For Detection Of Thyroid Blocking Immunoglobulins (TBI), (B) Assays For Dual Detection Of Thyroid Blocking Immunoglobulins (TBI) and Thyroid Stimulating Immunoglobulins (TSI), and (C) Kits.

A. Assays for Detection of Thyroid Blocking Immunoglobulin (TBI)

The invention provides methods for detecting thyroid hormone blocking immunoglobulin (TBI) in a test sample, comprising a) providing i) transgenic cells stably transfected with one or more expression vector comprising a 1) a reporter gene (e.g., luciferase gene) operably linked to a cAMP-inducible promoter, and 2) a chimeric TSH receptor (TSHR) gene operably linked to a constitutive promoter, wherein the cells express a chimeric TSHR on the cell membrane, ii) thyroid stimulating hormone (TSH) (e.g., bTSH), and iii) a control sample, and iv) a test sample (e.g., suspected of containing TBI), b) contacting the transgenic cells and the TSH with i) the control sample to produce a first sample, and ii) the test sample to produce a second sample, wherein the contacting is under conditions for binding of the TSH to the chimeric TSHR, and c) measuring the level of expression of the reporter gene in the first sample and in the second sample, wherein a reduced level of expression of the reporter gene in the second sample compared to the first sample indicates the presence of TBI in the test sample.

In one embodiment, the invention's TBI assay is a cell-based immunoglobulin competition assay, by which the thyroid blocking immunoglobulin competes with thyroid stimulating hormone (TSH) to bind to the TSH receptor (TSHR) expressed on the exemplary CHO-MC4 cells. In some embodiments, the TBI assay comprises using CHO-MC4 cells, cell growth medium, bTSH, Thyretain™ reaction buffer (Quidel Corp. & Diagnostic Hybrids, Inc., Ohio, USA), luciferase substrate and patient blood serum sample. The reagents and components of the invention's TBI assay are available to one of skill in the art (Thyretain™ assay; Quidel Corp. & Diagnostic Hybrids, Inc.).

The invention's assay is exemplified in Example 1. The exemplary CHO-MC4 cells of the invention's TBI assay are genetically engineered Chinese hamster ovary (CHO) cells expressing a chimeric human/rat TSHR and luciferase reporter gene driven by Glycoprotein hormone alpha subunit promoter. CHO-MC4 cells are used in Thyretain™ assay (Quidel Corp. & Diagnostic Hybrids, Inc.).

The invention's methods are useful for the diagnosis of diseases that are associated with the presence of TBI, such as Graves' disease, Hashimoto's thyroiditis (Endo et al. (1978) J. Clin. Endocrinology & Metabolism 46(5):734-739; Takasu et al. (1987) J. Clin. Endocrinology & Metabolism 64(2):239-245); Hypothyroidism (Takasu et al. (1984) J. Clin. Endocrinology & Metabolism 599(1):142-146); Neonatal hypothyroidism (Iseki et al. (1983) 57(2):384-387; Matsuura et al. (1980) The New England Journal of Medicine 303(13):738-741); Nongoitrous hypothyroidism (Arikawa et al. (1985) J. Clin. Endocrinology & Metabolism 60(5):953-959); Euthyroid or hypothyroid autoimmune thyroiditis (Chiovato et al. (1990) 71:40-45); Primary myxedema (Drexhage et al. (1980) Nature 289:594-596; Konishi et al. (1983) J. Clin. Endocrinology & Metabolism 57(3):544-549); and Idiopathic myxedema (Kohn et al. (2003) Autoimmunity 36:331-337).

The invention's methods are also useful for monitoring the progress of disease and/or treatment regimens, therapeutics, vaccines, etc. and in assisting clinicians in making treatment decisions.

The art described assays for thyroid hormone autoantibodies using the MC4 chimeric receptor that is also used in the instant invention (U.S. Pat. Appl. Publication no. US 2008-0187942, published on Aug. 7, 2008). However, the invention's methods were surprising because the art's assays were designed to measure thyroid hormone stimulating (not blocking) immunoglobulins (TSI) based on the view that the MC4 chimeric receptor is responsive only to stimulating antibodies, and that binding of the thyroid hormone blocking antibodies is either eliminated and/or reduced. Additionally, the art stated that the specificity of its methods for detecting TSI is a result of using cells that express the chimeric MC4 receptor, which provides greater specificity than a wild-type receptor by preferentially binding to stimulating autoantibodies (i.e., as opposed to blocking autoantibodies). Also, the art stated that the sensitivity of its methods for detecting TSI is a result of using cells that express the chimeric MC4 receptor, which provides greater sensitivity than a wild-type receptor by preferentially binding to stimulating autoantibodies (i.e., as opposed to blocking autoantibodies).

In addition to the surprising aspect of the invention's methods in detecting TBI, the invention's methods provide the surprising advantage of being sensitive for detecting TBI. Thus in one embodiment, the invention's methods of detecting TBI has a TBI $IC_{50}$ from 5 fold to 15 fold smaller (most preferably 7.5 fold smaller) than the TBI $IC_{50}$ when detecting TBI in the method that comprises substituting the transgenic cells that express the chimeric TSHR with cells that express a wild type TSHR. Data herein demonstrates that the chimeric TSHR expressed by CHO-MC4 cells is more useful than wild type TSHR in detecting TBI (Examples 2 and 4). For example, data herein demonstrate a higher sensitivity in detecting TBI when using CHO-MC4 cells that express a chimeric TSHR compared to H10 cells that express wild type TSHR; $IC_{50}$ of CHO-MC4 cells was 7.5 times smaller than that of H10 cells.

Another surprising advantage with respect to the invention's sensitivity for detecting TBI is that the invention's methods have TBI $IC_{50}$ from 10 fold to 30 fold smaller (most preferably 22 fold smaller) than the TBI $IC_{50}$ when detecting TBI in a method that comprises detecting specific binding of TBI with anti-TBI monoclonal antibody (such as in an ELISA assay). Data herein show that the $IC_{50}$ of the invention's TBI assay that uses CHO-MC4 cells is 1.344 ng/ml, which is 22 times lower than that of TRAb assay (Examples 3 and 4).

The above-discussed sensitivity of the invention's methods was surprising, at least in part, because the prior art's chimeric receptor TSHR-LH/CGR in which the TSH receptor (TSHR) is linked to rat luteotropin-chorionic gonadotropin (LH-CG) receptor was reported to be sensitive to TSI but to be very insensitive to TBI (Tahara et al. (1991) BBRC 179:70-77; Tahara et al. (1997) Thyroid 7(6):867-877). Furthermore, the prior art suggested that the MC4 chimeric receptor TSHR-LH/CGR that is expressed by the invention's exemplary transgenic cells (e.g., CHO-MC4 cells and RD-MC4 cells) lacked the epitope for TBI, while retaining the epitopes for TSI (Kohn et al. (2003) Autoimmunity 36:331-337; Sanders et al. (2011) J. Molecular Endocrinol. 46; 81-99).

While not necessary, in one embodiment, the invention's methods further comprise d) detecting a reduced level of expression of the reporter gene (e.g., luciferase gene) in the second sample compared to the first sample.

Also, while not required, in one embodiment, the invention's methods further comprises determining the level of TBI in the test sample. This may be done by, for example, comparing 1) the level of expression of the reporter gene after the contacting with the test sample, with 2) the level of expression of the reporter gene after contacting the transgenic cells with one or more standard samples, each containing a known concentration of TSH.

A further surprising aspect of the invention's methods is that they are TBI specific. A method for detecting the presence of TBI in a sample is referred to a as being "specific for TBI" or as being "TBI specific" where the method includes detecting inhibition, by TBI, of the specific binding of TSH to it receptor (TSHR such as a chimeric TSHR), and where the level of inhibition by TBI is not substantially altered (i.e., not increased by from 1% to 10%, or decreased by from 1% to 10%) by the presence of one or more of luteinizing hormone (LH), human chorionic gonadotropin (hCG), and follicle stimulating hormone (FSH).

For example, data herein demonstrate that the invention's TBI assay was specific to bTSH in that there was no substantial cross-reactivity or interference with TBI inhibition of the binding of TSH with TSHR when the three glycoprotein hormones LH, hCG, and FSH were tested in the invention's TBI assay at their highest biological normal range concentration and at two times their highest biological normal range concentration (Example 5). More particularly, whereas the invention's assays detected 86% inhibition by TBI, mixtures containing TBI with any one of LH, hCG, and FSH detected a range of from 81% to 84% inhibition.

While not intending to limit the range of concentration of TSH in the invention's assays, in one embodiment, TSH has a concentration of less than 100 mIU/ml, and more preferably from 0.2 mIU/ml to 100 mIU/ml. FIG. 1B shows that that the relationship between expression of the bioluminescence gene (e.g., luciferase gene) and TSH concentration is linear when the TSH concentrations are equal or lower than 100 mIU/ml.

It is not intended that the transgenic cells used in the invention's methods contain any particular reporter gene. However, in one embodiment, the reporter gene expresses a bioluminescence protein, such as a protein that comprises *Renilla* luciferase amino acid sequence SEQ ID NO:03.

It is not intended that the transgenic cells used in the invention's methods be limited to any particular type. However, in one embodiment, the transgenic cells comprise a cell exemplified by CHO-MC4 cell and RD-MC4 cell.

In one embodiment, the invention's methods may be performed by replacing TSH with a thyroid stimulating monoclonal antibody (such as M22) and/or with a thyroid stimulating polyclonal antibody (FIG. 9). Data herein demonstrate that the invention's TBI assay can detect the ability of exemplary sample 18HM to block stimulation by bTSH and/or thyroid stimulating immunoglobulin (TSI) (FIG. 10).

B. Assays for Dual Detection of Thyroid Blocking Immunoglobulin (TBI) and Thyroid Stimulating Immunoglobulin (TSI)

The invention provides methods for detecting thyroid hormone blocking immunoglobulin (TBI) and thyroid hormone stimulating immunoglobulin (TSI) in a test sample, comprising a) providing i) transgenic cells stably transfected with one or more expression vector comprising a 1) a reporter gene (e.g., luciferase gene) operably linked to a cAMP-inducible promoter, and 2) a chimeric TSH receptor (TSHR) gene operably linked to a constitutive promoter, wherein the cells express a chimeric TSHR on the cell membrane, ii) thyroid stimulating hormone (TSH), and iii) a control sample, iv) a test sample (e.g., suspected of containing TBI and/or TSI), b) contacting the transgenic cells and the TSH with i) the control sample to produce a first sample, and ii) the test sample to produce a second sample, wherein the contacting is under conditions for binding of the TSH to the chimeric TSHR, and c) measuring the level of expression of the reporter gene (e.g., by detecting bioluminescence resulting from luciferase enzyme activity) in the transgenic cells before the contacting and after the contacting, wherein i) a reduced level of expression of the reporter gene in the second sample compared to the first sample indicates the presence of TBI in the test sample, and ii) an increased level of expression of the reporter gene in the second sample compared to the first sample indicates the presence of TSI in the test sample.

Data herein in Examples 6-8 Demonstrate the use of the invention's assays to detect both TBI and TSI, including detection in serum samples (Table 8).

The invention's methods for dual detection of both TBI and TSI are useful for the diagnosis of diseases that are associated with the presence of TSI, such as Grave's disease and hyperthyroidism, for monitoring progress of disease and/or treatment, and for assisting clinicians in making treatment decisions.

While not intending to limit the transgenic cells to any particular type, in one embodiment, the transgenic cells comprise a cell exemplified by CHO-MC4 cell and RD-MC4 cell.

C. Kits

The invention provides kits for assisting in practicing the invention's methods. In one embodiment, the kit comprises i) transgenic cells stably transfected with one or more expression vector comprising a 1) a reporter gene operably linked to a cAMP-inducible promoter, and 2) a chimeric TSH receptor (TSHR) gene operably linked to a constitutive promoter, wherein the cells express a chimeric TSHR on the cell membrane, and ii) instructions for using the transgenic cells for detecting thyroid hormone blocking immunoglobulin (TBI).

The term "kit" is used in reference to a combination of reagents and other materials. It is contemplated that the kit may include reagents such as buffering agents, protein stabilizing reagents, signal producing systems (e.g., bioluminescence and/or fluorescence generating systems), antibodies, control samples, as well as testing containers (e.g., microtiter plates, etc.).

In one embodiment, the kit comprises a positive control sample that contains thyroid hormone blocking immunoglobulin (TBI). In another embodiment, the kit comprises thyroid stimulating hormone (TSH).

Where dual detection of both TBI and TSI is desired, the Kit may further comprise instructions for detecting thyroid hormone stimulating immunoglobulin (TSI) in a test sample. In another embodiment, the kit may further comprise a positive control sample that contains detecting thyroid hormone stimulating immunoglobulin (TSI).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); or L (liters); ml (milliliters); μl (microliters); μ (micro); m (milli); IU (International Units); cm (centimeters); mm (millimeters); μm (micrometers); nm (nanometers); ° C. (degrees Centigrade); sec. or s (second(s)); min. and m (minute(s)); MW (molecular weight); thyroid stimulating hormone or thyrotropin (TSH); bTSH (bovine TSH); TSI (thyroid stimulating immunoglobulin); TSAb (thyroid stimulating antibodies); EDTA (ethylene diamine tetraacetic acid); RLU/sec (relative light units per second); GM or PM (Growth Medium or Planting Medium); SM (Starvation Medium); HBSS (Hank's Balanced Salt Solution); EMEM (Eagle's Minimum Essential Medium); FBS or FCS (fetal bovine serum or fetal calf serum); DMSO (dimethyl sulfoxide); CHO (Chinese hamster ovary cells); CHO-R(CHO cells transfected with the human TSH receptor; CHO-Rluc (CHO-R cells transfected with the cre-luciferase reporter gene complex); Oxoid (Oxoid, Basingstoke, England); BBL (Becton Dickinson Microbiology Systems, Cockeysville, Me.)); DIFCO (Difco Laboratories, Detroit, NiI); U.S. Biochemical (U.S. Biochemical Corp., Cleveland, Ohio); Fisher (Fisher Scientific, Pittsburgh, Pa.); Sigma (Sigma Chemical Co., St. Louis, Mo.); ATCC (American Type Culture Collection, Rockville, Md.); LTI (Life Technologies, Rockville, Md.); and Promega (Promega Corp., Madison, Wis.).

In the following methods, all solutions used in these methods were sterile (with the exception of TSH, controls, patient specimens) and treated aseptically. All manipulations were conducted in a biosafety cabinet under aseptic conditions. Cell culture media (e.g., Ham's F-12, EMEM, etc.) were obtained from LTI, while additive reagents such as non-essential amino acids were obtained from Sigma.

Freezer vials of cells should not be allowed to warm from their −80° C. (or lower) storage temperature until immediately prior to thawing and use in the methods of the present invention, as cycling of the temperature may result in viability losses. Because it contains dithiothreitol, which is unstable at room temperatures, the 5× cell lysis solution should be removed from its −20° C. storage temperature only long enough to remove the required volume for preparation of the 1× solution. As it also contains dithiothreitol, reconstituted luciferase substrate solution should be kept frozen at −20° C. until just prior to use, at which time it may be removed and placed in a 25-37° C. water bath to thaw and reach room temperature.

In general, when removing liquid from wells (e.g., microtiter plates, etc.), the liquid may be dumped from the wells into a receptacle in a biosafety hood. The residual liquid can be drained and removed by placing the plate upside down on a sterile, absorbent wipe. Or, the liquid may be removed by aspiration using a fine tip on the aspirator. If aspiration is used, the plate is held at a steep angle so that the liquid does not overflow the wells, and the aspirator tip is directed down the side of the well almost to the bottom to remove the liquid and only leave minimal residue. However, care must be exercised in order to prevent disturbance of the cell monolayer, as the cells can be easily removed by the aspirator.

As indicated in the methods below, it is recommended, but not required that specimens, standards, and controls be run in triplicate. Because of the viscous nature of Solution 3 and the difficulty in achieving adequate mixing in the wells, the best reproducibility was achieved when the total triplicate volume is +10% (33 μl) of these reagents is transferred to the required triplicate volume+10% (330 μl) of Solution 3, thoroughly mixed, and 110 μl transferred to the triplicate wells.

In the preparation of cell monolayers (e.g., within the wells of microtiter plates), it is preferred that the cells be distributed evenly within the wells. Thus, in order to avoid uneven cell distributions, the transfer of cell suspensions into wells should be performed in a vibration-free biosafety hood. After all of the wells in a plate have received cells, the plate is covered and carefully placed on a solid, vibration-free surface, for 30 minutes, to allow the cells to attach undisturbed, to the bottom of the wells. This helps ensure that an even distribution of cells is present in each of the wells.

Example 1

Methods for Detecting TBI in a Sample

A stably transfected cell line (CHO-MC4) expressing a chimeric TSH-receptor (TSHR) and a CRE-dependent luciferase for detecting thyroid-stimulating immunoglobulins (TSI bioassay, Thyretain™) was previously described (U.S. Pat. Appl. Publication no. US 2008-0187942, published on Aug. 7, 2008). To develop a complementary thyroid-blocking antibody (TBI) bioassay, we compared the performance of the chimeric TSHR to a wild type (wt) TSHR.

CHO cells expressing a wt or chimeric TSHR and a CRE-dependent luciferase were isolated. Cells were grown at 37° C. for 15-18 hours and then incubated with bTSH, TSI, TBI, and/or patient serum. Luciferase expression was measured after incubation for 3 hours. Blocking activity was defined as percent inhibition of luciferase expression relative to induction with bTSH alone.

Both chimeric and wt cell lines showed induction of luciferase in response to bTSH in a dose-dependent manner, but displayed different levels of sensitivity and maximal induction. The wt TSHR-expressing cell line responded to concentrations of bTSH between 0.8 and 50 mIU/L, whereas the chimeric TSHR-expressing cell line had a wider dynamic range (1.6 to 200 mIU/L) and was induced to 8-fold higher levels. Both cell lines detected TSI in serum from patients with Graves' disease. When the cell lines were stimulated with either TSI or bTSH, luciferase expression was reduced in a dose-dependent manner by the addition of increasing concentrations of a blocking MAb, K1-70 (RSR, Cardiff, U.K.) or serum containing TBI. The chimeric cell line was more sensitive in that the inhibitory concentration 50% (IC50) of K1-70 was 3 to 5-fold lower on the chimeric cell line. Also, in contrast to the wt cell, the chimeric cell line displayed 3-4-fold higher inhibitory activity when tested with TBI-positive sera and uniformly displayed sigmoidal dose-response curves with serially diluted blocking sera. The results show that, compared to the wt, the chimeric TSHR cell line performs better and is a unique vehicle to develop both stimulating and blocking bioassays.

A. Exemplary Protocol for Detecting TBI in Serum Samples:
1. Coat one black, flat/clear-bottomed 96-well plate with 100 µl/well of Cell Attachment Solution (e.g., described in U.S. Pat. Appl. Publication No. US 2008-0187942, and commercially available as Thyretain™ Cell Attachment Solution from Quidel Corp. & Diagnostic Hybrids, Inc., Ohio, USA). Let solution remain on the wells for 30 seconds and then decant the solution.
2. Add 1 freezer vial of CHO MC4 cells to 5 ml of Thyretain™ Growth Media (e.g., described in U.S. Pat. Appl. Publication No. US 2008-0187942, and commercially available as Thyretain™ Growth Media from Quidel Corp. & Diagnostic Hybrids, Inc., Ohio, USA).
3. Plant cells at 100 µl/well in a 48-well format (skip the top and bottom rows of the plate and the first two columns on the left-hand and right-hand sides of the plate).
4. Incubate the plate of cells for 16-18 hours at 37° C.
5. At the end of the overnight growth period, microscopically inspect the cells for confluence and confirm that the cells are free of contaminants. Place the plate back into the incubator.
6. Prepare 4000 U/ml bTSH (this will allow for a 100 µIU/ml final concentration of bTSH in each well). This is your working stock.
7. Prepare a 1:11 dilution of each sample with bTSH—40 µL of each sample, 220 µL of 400 µIU/ml bTSH, and 180 µL Thyretain™ Reaction Buffer (e.g., described in U.S. Pat. Appl. Publication No. US 2008-0187942, and commercially available as Thyretain™ Reaction Buffer from Quidel Corp. & Diagnostic Hybrids, Inc., Ohio, USA).
8. Prepare the blank control by diluting normal serum 1:11 in reaction buffer (40 µL serum and 400 µL Reaction Buffer).
9. Prepare the bTSH control by diluting 400 of normal serum, 220 µl of 400 µIU/ml bTSH, and 180 µL Thyretain™ Reaction Buffer.
Note: The plate preferably also contains replicate wells containing Thyretain™ Reaction Buffer only.
10. Remove plate from incubator and rinse and then re-feed the cells with 100 µl/well of Thyretain™ Reaction Buffer.
11. Add the prepared samples to the cells in triplicate at 1000/well
12. Incubate the cells at 37° C. for 3 hours.
13. Decant the contents of all wells after 3 hours incubation
14. Add 75 µl/well Bright-Glo™ to each well
15. Incubate the cells at room temperature for 10 minutes and then read the plate on a Veritas™ plate reader B. Exemplary TSH Concentration in the TBI Assay:
FIG. 1 shows the bTSH dose response curves using the CHO-MC4 cells. FIG. 1A shows luciferase induction with a serial two fold dilution of the bTSH in a concentration range from 0.2 mIU/ml to 400 mIU/ml; FIG. 1B shows luciferase induction with the bTSH in a narrower concentration range from 0.2 mIU/ml to 100 mIU/ml. The ratio of S/B refers the luciferase signal-to-background ratio, which normalizes the luciferase activity (as measured in RLU) generated from different experiments.

FIG. 1A shows that the luciferase induction increases with bTSH concentration. The relationship between the luciferase induction and bTSH concentration is linear when the bTSH concentrations are equal or lower than 100 mIU/ml. When the concentrations of bTSH are higher than 100 mIU/ml, the increase of the luciferase activity declines and the induction gradually approaches but does not quite reach a plateau. FIG. 1B zooms in on the linear portion of FIG. 1A, when the bTSH concentrations equal or lower than 100 mIU/ml. The $R^2$ (coefficient value) is close to one.

In the TBI assay, the thyroid blocking antibody competes with the bTSH for the binding of the TSH receptor located on the cell membrane. Therefore, the concentration of bTSH is an important component for determination of the assay sensitivity. The bTSH concentrations in the linear range for the luciferase induction, shown in FIG. 1B, have higher detection sensitivity than the higher nonlinear concentrations of bTSH. Within the linear range of concentration of bTSH, the highest concentration may be used as one optimal concentration for the assay. Although all of the linear concentrations have the same bTSH detection sensitivity, higher bTSH concentrations mean larger signal-to-background ratios.

Example 2

The Chimeric TSHR is More Useful than the Wild Type TSHR in Detecting TBI

A. Comparison of Detection Sensitivity of Thyroid Blocking Immunoglobulin (TBI) Assays with K1-70 Thyroid Blocking Monoclonal Antibody (MAb) in MC4 and TSHRwt Cells (H10)

A serially diluted thyroid blocking MAb K1-70, from 0.1 to 100 ng/ml, was tested with TBI assay in CHO-MC4 cells or H10 cells. The results are shown in FIG. 3.

All sample data were normalized with the background RLU of reaction buffer with 1:11 diluted normal serum. The percentage (%) inhibition was calculated as: (bTSH control RLU—sample RLU)/bTSH control RLU.

The results show that CHO-MC4 cells have much higher detection sensitivity to K1-70 than H10 cells. $IC_{50}$ of CHO-MC4 cells was 7.5 times smaller than that of H10 cells.

B. Comparison of Detection Sensitivity of TBI Assay with a Blocking Antibody Containing Serum in MC4 and H10 Cells Serum of one TBI positive patient was serially diluted from 1:22 to 1:90,000 and tested by TBI assay in MC4 or H10 cells. The results are shown in FIG. 4.

The results showed a sigmoidal curve of the percentage inhibition of serum dilution in CHO-MC4 cells, which is similar to that of the K1-70 in the previous experiment. However, it did not show the same curve in the H10 cells.

This result confirms the CHO-MC4 cells are more sensitive in detecting TBI than H10 cells.

Example 3

The Sensitivity of the Invention's TBI Assay is Higher than Competitive Binding Methods, Such as Kronus™ ELISA Assay We conducted a comparison of thyroid blocking monoclonal antibody K1-70 dose response curves to compare the invention's TBI assay with the prior art's competitive binding methods, such as Kronus™ ELISA assay (TRAb assay). In this experiment, K1-70 stimulating monoclonal antibody is tested on both TBI assay in CHO-MC4 cells and TRAb assay (Kronus™). The results are shown in FIG. 5.

The results show that the $IC_{50}$ of TBI assay with CHO-MC4 cells is 1.344 ng/ml, which is 22 times lower than that of TRAb assay, indicating CHO-MC4 cells have higher TBI detecting sensitivity than the TRAb assay.

Example 4

Sensitivity of the Invention's TBI Assays

The following data compares the sensitivity of the inventions assays in detecting TBI with other assays.

TABLE 1

Dilution response of TBI positive serum sample

| Dilutions | 2800 | 2400 | 2000 | 1800 | 1600 | 1400 | 1200 | 1000 | 800 | 640 | 500 | 320 | 160 | 80 | 40 |
|---|---|---|---|---|---|---|---|---|---|---|---|---|---|---|---|
| RLU | 13418 | 13351 | 13140 | 12600 | 12114 | 11008 | 10235 | 10657 | 9970 | 9073 | 7474 | 6120 | 3689 | 2937 | 2807 |
| % inhibition | 6% | 7% | 9% | 14% | 19% | 29% | 37% | 33% | 39% | 48% | 63% | 75% | 98% | 105% | 107% |

TABLE 2

Dose response of thyroid blocking monoclonal antibody K1-70

| ng/ml | 0.0025 | 0.05 | 0.1 | 0.2 | 0.4 | 0.6 | 0.8 | 1 | 1.5 | 2 | 2.5 | 5 | 10 |
|---|---|---|---|---|---|---|---|---|---|---|---|---|---|
| RLU | 16354 | 15651 | 13630 | 14144 | 12804 | 12600 | 12708 | 11341 | 9422 | 7940 | 6617 | 4008 | 2700 |
| % inhibition | −6% | 0% | 18% | 13% | 25% | 27% | 26% | 38% | 55% | 68% | 79% | 102% | 114% |

TABLE 3

Comparison of TBI positive serum dilution results on TBI and TRAb assay

| Dilutions | | 44 | 88 | 176 | 352 | 704 | 1408 | 2816 | 5632 | 11264 | 22528 | 45056 | 90112 |
|---|---|---|---|---|---|---|---|---|---|---|---|---|---|
| % inhibition | TBI assay | 95% | 96% | 89% | 65% | 25% | 15% | 1% | −2% | 0% | −4% | −5% | −5% |
| | TRAb assay | 73% | 50% | 26% | 9% | 14% | 2% | −10% | −7% | −4% | 3% | −8% | −3% |

TABLE 4

Comparison of thyroid blocking monoclonal antibody K1-70 dose response on TBI and TRAb assay

| K1-70 | (ng/ml) | 100 | 50 | 25 | 12.5 | 6.25 | 1.56 | 0.4 | 0.1 |
|---|---|---|---|---|---|---|---|---|---|
| % inhibition | TBI assay | 101% | 103% | 104% | 104% | 99% | 60% | 21% | 6% |
| | TRAb assay | 81% | 68% | 46% | 31% | 18% | 14% | 13% | 11% |

Example 5

Specificity of the Invention's TBI Assay

Tables 5 and 6 show the results of the specificity tests of the invention's TBI assay with the glycoprotein hormone subfamily—luteinizing hormone (LH), human chorionic gonadotropin (hCG), and follicle stimulating hormone (FSH). In the experiments, two concentrations of each hormone were tested. One concentration is the highest level within the normal range; the other is the twice that concentration. K1-70 thyroid blocking monoclonal antibody was used as positive control; the hormones were tested with K1-70 in the reaction buffer.

The normal ranges of each hormone in a human are as follows: LH 5-20 mIU/ml; hCG 0.1-8000 mIU/ml; FSH 1.4-116.3 mIU/ml.

TABLE 5

Luciferase induction with the glycoprotein hormones tested with the highest normal range concentration in CHO-MC4 cells

|  |  | RLU | % inhibition |
|---|---|---|---|
| TBI positive | 2.5 ng K1-70 | 5532 | 86% |
| FSH 116.3 mIU/ml | 2.5 ng K1-70 | 6101 | 81% |
|  | Reaction buffer | 16489 | 0% |
| LH 20 mIU/ml | 2.5 ng K1-70 | 6102 | 81% |
|  | Reaction buffer | 17263 | −5% |
| hCG 8000 mIU/ml | 2.5 ng K1-70 | 5998 | 82% |
|  | Reaction buffer | 17502 | −7% |

TABLE 6

Luciferase induction with the glycoprotein hormones tested with two times the highest normal range concentration in CHO-MC4 cells

|  |  | RLU | % inhibition |
|---|---|---|---|
| TBI positive | 2.5 ng K1-70 | 5532 | 86% |
| FSH 232.6 mIU/ml | 2.5 ng K1-70 | 5811 | 83% |
|  | Reaction buffer | 16272 | 1% |
| LH 40 mIU/ml | 2.5 ng K1-70 | 5773 | 84% |
|  | Reaction buffer | 17368 | −6% |
| hCG 16000 mIU/ml | 2.5 ng K1-70 | 5947 | 82% |
|  | Reaction buffer | 16483 | 0% |

The data demonstrate that there was no substantial cross-reactivity or interference when the three glycoprotein hormones were tested in the TBI assay. These results indicate that the TBI assay is very specific to bTSH.

Example 6

The Invention's Dual Bioassay Methods can Successfully Detect Both TBI and TSI Here we describe an assay for detection of both thyroid-stimulating immunoglobulins (TSI) and thyroid-blocking immunoglobulins (TBI) using the same transgenic cell CHO cell line (CHO-MC4) that expresses a chimeric TSH-receptor (TSHR), and that was described in U.S. Pat. Appl. Publication no. US 2008-0187942, published on Aug. 7, 2008.

Methods:

To detect blocking activity CHO-MC4 cells were induced with bovine TSH (bTSH) mixed with an anti-TSHR blocking MAb or human serum samples. Blocking activity was defined as percent inhibition of luciferase expression relative to induction with bTSH alone. MAbs K1-70 and M-22 were purchased from RSR (Cardiff, U.K.). All samples were also measured for TSHR autoantibody (TRAb) (ELISA, Kronus™) and TSI (Thyretain™).

Results:

Luciferase expression of bTSH-stimulated CHO-MC4 cells decreased in response to the blocking MAb K1-70 in a dose-dependent manner. Fifty euthyroid control sera demonstrated inhibition between 7 to 52% allowing us to establish a preliminary 95$^{th}$ percentile cut-off of 50% inhibition. TRAb-positive and TSI-negative sera from patients with autoimmune hypothyroidism reduced luciferase expression to background levels (100% inhibition). Serial dilution experiments demonstrated titers of blocking activity in these samples of up to 1:200. The TBI bioassay was over 20-fold more sensitive than the TRAb assay with the K1-70 MAb showing an IC50 of 1.34+/−0.09 ng/ml versus IC50 of 29.73+/−3.27 ng/ml.

The TBI bioassay was also capable of detecting TSI. Using a stimulating MAb (M-22) or TSI-positive sera, we observed luciferase expression above that seen with bTSH alone i.e. negative inhibition. The dose-response of M-22 stimulatory activity in both assays was essentially identical with 50% effective concentrations (EC50) of 0.14 ng/ml and 0.16 ng/ml in the TSI and TBI assays, respectively. Serial dilution of TSI-positive sera tested in both assays also showed equivalent dose-response curves.

A. TBI Assay with Serial Diluted M22 or TSI Positive Patient Serum

The thyroid stimulating monoclonal antibody M22, or TSI positive serum were serially diluted and tested using the invention's TBI assay using CHO-MC4 cells. The results are in FIG. 6. FIG. 6 shows that both dilution curves demonstrate that the invention's TBI assay can detect thyroid stimulating immunoglobulin (TSI).

B. Correlation Between the TSI and TBI Assay Using 171 TSI Positive Serum Samples In this experiment, 171 TSI positive sera were prepared and simultaneously tested on either TSI or TBI assays. The results are shown in FIG. 7.

The results show a high correlation between the TSI and TBI assay ($R^2=0.9$), indicating the TBI assay can be used for detecting TSI positive sera.

Example 7

The Invention's Dual Bioassay Methods can Differentiate Anti-TSHR Auto-Antibodies into Those that Stimulate the Thyroid and Those that Block Stimulation of the Thyroid In this experiment, the thyroid stimulating monoclonal antibody M22 and thyroid blocking monoclonal antibody K1-70 were mixed together with different ratios, such as 100:0, 90:10, 80:20, through 0:100 and tested on the invention's TBI assay using CHO-MC4 cells. The results are shown in FIG. 8.

FIG. 8 shows that when the portions of K1-70 in the mixture are increased from 0 to 100% (or M22 from 100 to 0 percent), the TBI % inhibitions are gradually increased from negative 100% to positive 100%. It indicates that in the TBI assay, it is not only able to detect the thyroid stimulation antibody, but also shows blocking antibody as a negative inhibition results.

Example 8

Sensitivity of the Invention's Dual Bioassay for Detecting TBI and/or TSI

The following results show the sensitivity of the invention's dual bioassay for detecting TBI and/or TSI in serum samples (Table 6) or when using monoclonal antibodies M22 and K1-70 (Tables 5 and 7).

TABLE 6

TBI assay with different ratios of thyroid stimulating monoclonal antibody M22 and thyroid blocking monoclonal antibody K1-70

| M22:K1-70 | *M22only 100% | 90:10 | 80:20 | 70:30 | 60:40 | 50:50 | 40:60 | 30:70 | 20:80 | 10:90 | **K1-70only 100% |
|---|---|---|---|---|---|---|---|---|---|---|---|
| RLU | 21151 | 20364 | 19557 | 17624 | 16713 | 14649 | 12252 | 8651 | 6467 | 3999 | 2415 |
| % inhibition | −106% | −98% | −89% | −68% | −59% | −37% | −11% | 27% | 51% | 77% | 94% |

*0.8 ng/ml M22
**5 ng/ml K1-70

TABLE 7

Comparison between TBI and TSI with TSI positive serum sample

| | TSI positive serum sample | | | | | | | | | | | |
|---|---|---|---|---|---|---|---|---|---|---|---|---|
| Dilution | 11 | 16 | 22 | 32 | 44 | 64 | 88 | 128 | 176 | 256 | 352 | 512 |
| RLU | 14712 | 13775 | 13213 | 12720 | 12076 | 10989 | 10356 | 10098 | 9571 | 9502 | 8999 | 9288 |
| % inhibition | −66% | −54% | 47% | −41% | −33% | −19% | −11% | −8% | −1% | −1% | 6% | 2% |
| SRR % | 261% | 235% | 209% | 163% | 123% | 92% | 78% | 66% | 61% | 52% | 51% | 49% |

TABLE 8

Comparison between TBI and TSI with thyroid stimulating monoclonal antibody M22

| | M22 stimulating antibody | | | | | | | | | | | | | | |
|---|---|---|---|---|---|---|---|---|---|---|---|---|---|---|---|
| ng/ml | 1.2 | 0.8 | 0.6 | 0.4 | 0.35 | 0.3 | 0.25 | 0.2 | 0.15 | 0.1 | 0.08 | 0.06 | 0.05 | 0.04 | 0.02 |
| RLU | 15702 | 14970 | 14415 | 14201 | 14135 | 14349 | 13142 | 13259 | 11715 | 11316 | 10891 | 10055 | 9690 | 9259 | 9066 |
| % inhibition | −83% | −73% | −66% | −64% | −63% | −65% | −50% | −52% | −32% | −27% | −21% | −11% | −6% | 0% | 2% |
| SRR % (TBI) | 365% | 368% | 368% | 332% | 315% | 302% | 283% | 270% | 236% | 180% | 146% | 122% | 111% | 95% | 61% |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method for detecting thyroid hormone blocking immunoglobulin (TBI) in a sample, comprising
a) combining
   i) transgenic cells stably transfected with one or more expression vector comprising a
      1) a first nucleic acid sequence that encodes a reporter, wherein said first nucleotide sequence is operably linked to a cAMP-inducible promoter, and
      2) the nucleotide sequence of SEQ ID NO: 2 that encodes a chimeric TSH receptor (TSHR), wherein said SEQ ID NO: 2 is operably linked to a constitutive promoter,
   wherein said cells express said chimeric TSHR on the cell membrane,
   ii) a thyroid stimulating polypeptide that stimulates said chimeric TSHR upon binding to said TSHR, wherein said thyroid stimulating polypeptide is selected from the group consisting of thyroid stimulating hormone (TSH), a thyroid stimulating monoclonal antibody, and thyroid stimulating polyclonal antibody, and
   iii) a sample, wherein said sample is a control sample or is a test sample,
wherein said combining said transgenic cells and said TSH with
   A) said control sample produces a first sample, and
   B) said test sample produces a second sample, and
is under conditions for binding of said TSH to said chimeric TSHR, and
b) measuring the level of expression of said reporter in said first sample and in said second sample, wherein a reduced level of expression of said reporter in said second sample compared to said first sample indicates the presence of TBI in said test sample.

2. The method of claim 1, wherein the $IC_{50}$ for TBI is from 5 fold to 15 fold smaller than the $IC_{50}$ for TBI when the method is performed with said transgenic cells in which chimeric TSHR is substituted with wild type TSHR.

3. The method of claim 1, wherein the $IC_{50}$ for TBI is from 10 fold to 30 fold smaller when the thyroid stimulating polypeptide is TSH than when the thyroid stimulating polypeptide is an anti-TBI monoclonal antibody.

4. The method of claim 1, wherein said method further comprises detecting a reduced level of expression of said reporter in said second sample compared to said first sample.

5. The method of claim 1, wherein said method further comprises determining the level of TBI in said test sample by comparing a) the level of expression of said reporter after said contacting with said test sample, with
b) the level of expression of said reporter after contacting said transgenic cells with one or more standard samples, each containing a known concentration of TSH.

6. The method of claim 1, wherein said method is TBI specific.

7. The method of claim 1, wherein said thyroid stimulating polypeptide is TSH and wherein said TSH is present in at least one of said first sample and said second sample at a concentration of 0.2 mIU/ml to 100 mIU/ml.

8. The method of claim 1, wherein said reporter comprises a bioluminescence protein.

9. The method of claim 8, wherein said bioluminescence protein comprises Renilla luciferase amino acid sequence SEQ ID NO:3.

10. The method of claim 1, wherein said transgenic cells are Chinese hamster ovary (CHO) cells or human Rhabdomyosarcoma (RD) cells.

11. The method of claim 1, wherein said thyroid stimulating polypeptide is a thyroid stimulating monoclonal antibody.

12. The method of claim 1, wherein said thyroid stimulating polypeptide is a thyroid stimulating polyclonal antibody.

13. A method for detecting thyroid hormone blocking immunoglobulin (TBI) and thyroid hormone stimulating immunoglobulin (TSI) in a sample, comprising
a) combining
   i) transgenic cells stably transfected with one or more expression vector comprising a
      1) a first nucleic acid sequence that encodes a reporter, wherein said first nucleic acid sequence is operably linked to a cAMP-inducible promoter, and
      2) the nucleotide sequence of SEQ ID NO: 2 that encodes a chimeric TSH receptor (TSHR), wherein said SEQ ED NO: 2 is operably linked to a constitutive promoter,
   wherein said cells express said chimeric TSHR on the cell membrane,
   ii) a thyroid stimulating hormone (TSH),
   iii) a control sample or a test sample,
wherein combining said transgenic cells and said TSH with
   A) said control sample produces a first sample, and
   B) said test sample produces a second sample,
combining is under conditions for binding of said TSH to said chimeric TSHR, and
b) measuring the level of expression of said reporter in said transgenic cells before said combining and after said combining, wherein i) a reduced level of expression of said reporter in said second sample compared to said first sample indicates the presence of TBI in said test sample, and ii) an increased level of expression of said reporter in said second sample compared to said first sample indicates the presence of TSI in said test sample.

14. The method of claim 13, wherein said method further comprises detecting a reduced level of expression of said reporter in said second sample compared to said first sample, wherein said detecting of a reduced level of expression of said reporter indicates the presence of TBI in said test sample.

15. The method of claim 13, wherein said transgenic cells are Chinese hamster ovary (CHO) cells or human Rhabdomyosarcoma (RD) cells.

\* \* \* \* \*

SEQUENCE LISTING

<160> NUMBER OF SEQ ID NOS: 4

<210> SEQ ID NO 1
<211> LENGTH: 730
<212> TYPE: PRT
<213> ORGANISM: Artificial Sequence
<220> FEATURE:
<223> OTHER INFORMATION: Synthetic

<400> SEQUENCE: 1

```
Met Arg Pro Ala Asp Leu Leu Gln Leu Val Leu Leu Asp Leu Pro
1               5                   10                  15

Arg Asp Leu Gly Gly Met Gly Cys Ser Ser Pro Cys Glu Cys His
                20                  25                  30

Gln Glu Glu Asp Phe Arg Val Thr Cys Lys Asp Ile Gln Arg Ile Pro
                35                  40                  45

Ser Leu Pro Pro Ser Thr Gln Thr Leu Lys Leu Ile Glu Thr His Leu
50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
                100                 105                 110

Asn Leu Thr Tyr Ile Asp Pro Asp Ala Leu Lys Glu Leu Pro Leu Leu
                115                 120                 125

Lys Phe Leu Gly Ile Phe Asn Thr Gly Leu Lys Met Phe Pro Asp Leu
                130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
                180                 185                 190

Gln Gly Tyr Ala Phe Asn Gly Thr Lys Leu Asp Ala Val Tyr Leu Asn
                195                 200                 205

Lys Asn Lys Tyr Leu Thr Val Ile Asp Lys Asp Ala Phe Gly Gly Val
                210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Thr Leu Pro Ser Lys Glu Lys Phe Thr Ser Leu
                260                 265                 270

Leu Val Ala Thr Leu Thr Tyr Pro Ser His Cys Cys Ala Phe Ser Asn
                275                 280                 285

Leu Pro Lys Lys Glu Gln Asn Phe Ser Phe Ser Ile Phe Glu Asn Phe
                290                 295                 300

Ser Lys Gln Cys Glu Ser Thr Val Arg Lys Ala Asp Asn Glu Thr Leu
305                 310                 315                 320

Tyr Ser Ala Ile Phe Glu Glu Asn Glu Leu Ser Gly Trp Asp Glu Leu
                325                 330                 335

Lys Asn Pro Gln Glu Glu Thr Leu Gln Ala Phe Asp Ser His Tyr Asp
                340                 345                 350

Tyr Thr Ile Cys Gly Asp Ser Glu Asp Met Val Cys Thr Pro Lys Ser
```

355                 360                 365
Asp Glu Phe Asn Pro Cys Glu Asp Ile Met Gly Tyr Lys Phe Leu Arg
            370                 375                 380

Ile Val Val Trp Phe Val Ser Leu Leu Ala Leu Leu Gly Asn Val Phe
385                 390                 395                 400

Val Leu Leu Ile Leu Leu Thr Ser His Tyr Lys Leu Asn Val Pro Arg
                405                 410                 415

Phe Leu Met Cys Asn Leu Ala Phe Ala Asp Phe Cys Met Gly Met Tyr
            420                 425                 430

Leu Leu Leu Ile Ala Ser Val Asp Leu Tyr Thr His Ser Glu Tyr Tyr
                435                 440                 445

Asn His Ala Ile Asp Trp Gln Thr Gly Pro Gly Cys Asn Thr Ala Gly
            450                 455                 460

Phe Phe Thr Val Phe Ala Ser Glu Leu Ser Val Tyr Thr Leu Thr Val
465                 470                 475                 480

Ile Thr Leu Glu Arg Trp Tyr Ala Ile Thr Phe Ala Met Arg Leu Asp
                485                 490                 495

Arg Lys Ile Arg Leu Arg His Ala Cys Ala Ile Met Val Gly Gly Trp
            500                 505                 510

Val Cys Cys Phe Leu Leu Ala Leu Leu Pro Leu Val Gly Ile Ser Ser
                515                 520                 525

Tyr Ala Lys Val Ser Ile Cys Leu Pro Met Asp Thr Glu Thr Pro Leu
530                 535                 540

Ala Leu Ala Tyr Ile Val Phe Val Leu Thr Leu Asn Ile Val Ala Phe
545                 550                 555                 560

Val Ile Val Cys Cys Cys Tyr Val Lys Ile Tyr Ile Thr Val Arg Asn
                565                 570                 575

Pro Gln Tyr Asn Pro Gly Asp Lys Asp Thr Lys Ile Ala Lys Arg Met
            580                 585                 590

Ala Val Leu Ile Phe Thr Asp Phe Ile Cys Met Ala Pro Ile Ser Phe
                595                 600                 605

Tyr Ala Leu Ser Ala Ile Leu Asn Lys Pro Leu Ile Thr Val Ser Asn
610                 615                 620

Ser Lys Ile Leu Leu Val Leu Phe Tyr Pro Leu Asn Ser Cys Ala Asn
625                 630                 635                 640

Pro Phe Leu Tyr Ala Ile Phe Thr Lys Ala Phe Gln Arg Asp Val Phe
                645                 650                 655

Ile Leu Leu Ser Lys Phe Gly Ile Cys Lys Arg Gln Ala Gln Ala Tyr
            660                 665                 670

Arg Gly Gln Arg Val Pro Pro Lys Asn Ser Thr Asp Ile Gln Val Gln
            675                 680                 685

Lys Val Thr His Asp Met Arg Gln Gly Leu His Asn Met Glu Asp Val
            690                 695                 700

Tyr Glu Leu Ile Glu Asn Ser His Leu Thr Pro Lys Lys Gln Gly Gln
705                 710                 715                 720

Ile Ser Glu Glu Tyr Met Gln Thr Val Leu
                725                 730

<210> SEQ ID NO 2
<211> LENGTH: 2193
<212> TYPE: DNA
<213> ORGANISM: Artificial Sequence
<220> FEATURE:
<223> OTHER INFORMATION: Synthetic

<400> SEQUENCE: 2

```
atgaggccgg cggacttgct gcagctggtg ctgctgctcg acctgcccag ggacctgggc      60
ggaatggggt gttcgtctcc accctgcgag tgccatcagg aggaggactt cagagtcacc     120
tgcaaggata ttcaacgcat ccccagctta ccgcccagta cgcagactct gaagcttatt     180
gagactcacc tgagaactat tccaagtcat gcattttcta atctgcccaa tatttccaga     240
atctacgtat ctatagatgt gactctgcag cagctggaat cacactcctt ctacaatttg     300
agtaaagtga ctcacataga aattcggaat accaggaact taacttacat agaccctgat     360
gccctcaaag agctccccct cctaaagttc cttggcattt tcaacactgg acttaaaatg     420
ttccctgacc tgaccaaagt ttattccact gatatattct ttatacttga aattacagac     480
aaccctaca tgacgtcaat ccctgtgaat gcttttcagg gactatgcaa tgaaaccttg     540
acactgaagc tgtacaacaa tggctttact tcagtccaag gatatgcttt caatgggaca     600
aagctggatg ctgtttacct aaacaagaat aaatacctga cagttattga caaagatgca     660
tttgaggag tatacagtgg accaagcttg ctggacgtgt ctcaaaccag tgtcactgcc     720
cttccatcca aaggcctgga gcacctgaag gaactgatag caagaaacac ctggactctt     780
aagacactgc cctccaaaga aaattcacg agcctcctgg tcgccacgct gacctacccc     840
agccactgct gcgccttcag taatttgccg aagaagaac agaattttc attttccatt     900
tttgaaaact tctccaaaca atgcgaaagc acagttagaa aagcagataa cgagacgctt     960
tattccgcca tctttgagga gaatgaactc agtggctggg atgagctcaa aaaccccag    1020
gaagagactc tacaagcttt tgacagccat tatgactaca ccatatgtgg ggacagtgaa    1080
gacatggtgt gtacccccaa gtccgatgag ttcaacccgt gtgaagacat aatgggctac    1140
aagttcctga aattgtggt gtggttcgtt agtctgctgg ctctcctggg caatgtcttt    1200
gtcctgctta ttctcctcac cagccactac aaactgaacg tcccccgctt tctcatgtgc    1260
aacctggcct tgcggatttt ctgcatgggg atgtacctgc tcctcatcgc ctctgtagac    1320
ctctacactc actctgagta ctacaaccat gccatcgact ggcagacagg ccctgggtgc    1380
aacacgctg gtttcttcac tgtctttgca agcgagttat cggtgtatac gctgacggtc    1440
atcaccctgg agcgctggta tgccatcacc ttcgccatgc gcctggaccg gaagatccgc    1500
ctcaggcacg catgtgccat catggttggg ggctgggttt gctgcttcct tctcgccctg    1560
cttcctttgg tgggaataag tagctatgcc aaagtcagta tctgcctgcc catggacacc    1620
gagacccctc ttgctctggc atatattgtt tttgttctga cgctcaacat agttgccttc    1680
gtcatcgtct gctgctgtta tgtgaagatc tacatcacag tccgaaatcc gcagtacaac    1740
ccaggggaca aagataccaa aattgccaag aggatggctg tgttgatctt caccgacttc    1800
atatgcatgg ccccaatctc attctatgct ctgtcagcaa ttctgaacaa gcctctcatc    1860
actgttagca actccaaaat cttgctggta ctcttctatc cacttaactc ctgtgccaat    1920
ccattcctct atgctatttt caccaaggcc ttccagaggg atgtgttcat cctactcagc    1980
aagtttggca tctgtaaacg ccaggctcag gcataccggg ggcagagggt tcctccaaag    2040
aacagcactg atattcaggt tcaaaaggtt acccacgaca tgaggcaggg tctccacaac    2100
atggaagatg tctatgaact gattgaaaac tcccatctaa ccccaaagaa gcaaggccaa    2160
atctcagaag agtatatgca aacggttttg taa                                 2193
```

<210> SEQ ID NO 3
<211> LENGTH: 550

<212> TYPE: PRT
<213> ORGANISM: Renilla reniformis

<400> SEQUENCE: 3

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
    50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
        115                 120                 125
Ser Lys Lys Gly Leu Gln Lys Ile Leu Asn Val Gln Lys Lys Leu Pro
    130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
```

```
Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp Glu His Phe
        420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
        450                 455                 460

Phe Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 4
<211> LENGTH: 1653
<212> TYPE: DNA
<213> ORGANISM: Artificial Sequence
<220> FEATURE:
<223> OTHER INFORMATION: Synthetic

<400> SEQUENCE: 4
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccgttttaa tgaatacgat     540 tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780 cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctggggcgc acctctttcg     960 aaagaagtcg gggaagcggt tgcaaaacgc ttccatcttc cagggatacg acaaggatat    1020
gggctcactg agactacatc agctattctg attacccg aggggatga taaaccgggc    1080 gcggtcggta aagttgttcc attttttgaa gcgaaggttg tggatctgga taccgggaaa    1140
```

-continued

```
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653
```